United States Patent [19]
Cabri et al.

[11] Patent Number: 5,856,333
[45] Date of Patent: Jan. 5, 1999

[54] SUBSTITUTED CAMPTOTHECIN DERIVATIVES AND PROCESS FOR THEIR PREPARATION

[75] Inventors: Walter Cabri, Milan; Ilaria Candiani, Varese; Angelo Bedeschi, Milan; Franco Zarini, Milan; Sergio Penco, Milan, all of Italy

[73] Assignee: Pharmacia & Upjohn S.p.A., Milan, Italy

[21] Appl. No.: 776,192

[22] PCT Filed: May 10, 1996

[86] PCT No.: PCT/EP96/02008

§ 371 Date: Jan. 27, 1997

§ 102(e) Date: Jan. 27, 1997

[87] PCT Pub. No.: WO96/37496

PCT Pub. Date: Nov. 28, 1996

[30] Foreign Application Priority Data

May 26, 1995 [GB] United Kingdom .................. 9510716

[51] Int. Cl.$^6$ .................... C07D 491/22; A61K 31/435
[52] U.S. Cl. ................ 514/283; 514/279; 546/41; 546/48
[58] Field of Search ..................... 514/283; 546/48

[56] References Cited

U.S. PATENT DOCUMENTS

| | | | |
|---|---|---|---|
| 5,004,758 | 4/1991 | Boehm et al. | 514/283 |
| 5,122,606 | 6/1992 | Wani et al. | 546/41 |
| 5,340,817 | 8/1994 | Wall et al. | 514/279 |
| 5,401,747 | 3/1995 | Wall et al. | 546/48 |
| 5,602,141 | 2/1997 | Bedeschi et al. | 514/279 |
| 5,614,628 | 3/1997 | Cabri et al. | 546/48 |

FOREIGN PATENT DOCUMENTS

| | | |
|---|---|---|
| 0325247 | 7/1989 | European Pat. Off. . |
| 91-04260 | 4/1991 | WIPO . |

OTHER PUBLICATIONS

Kingsbury, J. Med. Chem. vol. 34 pp. 98–107 (1991).

*Primary Examiner*—Donald G. Daus
*Attorney, Agent, or Firm*—Oblon, Spivak, McClelland, Maier & Neustadt, P.C.

[57] ABSTRACT

The present invention relates to substituted camptothecin derivatives of formula (I) wherein the symbol - - - - represents a single or double bond; $R_1$, $R_2$ and $R_3$ are as defined under (a) or (b) below: (a) $R_1$ and $R_2$ are, each independently, hydrogen; $C_1-C_4$ alkyl; $C_3-C_7$ cycloalkyl; phenyl $C_1-C_6$ alkyl; an optionally substituted phenyl ring; —$NR_5R_6$ wherein one of $R_5$ and $R_6$ is hydrogen, $C_1-C_6$ alkyl or benzyl and the other is hydrogen, $C_1-C_6$ alkanoyl, an optionally substituted $C_1-C_6$ alkoxycarbonyl, an optionally substituted benzoyl, phenyl $C_1-C_6$ alkanoyl, an optionally substituted $C_1-C_6$ alkoxycarbonyl, an optionally substituted phenoxycarbonyl or phenyl $C_1-C_6$ alkoxycarbonyl, or $R_5$ and $R_6$, combined together with the nitrogen atom to which they are linked, form a 4–7 membered saturated, optionally substituted, heteromonocyclic ring residue; $COOR_8$ wherein $R_8$ is hydrogen, $C_1-C_6$ alkyl, $C_3-C_7$ cycloalkyl or phenyl $C_1-C_6$ alkyl; or $COR_9$ wherein Rg is $C_1-C_6$ alkyl, $C_3-C_7$ cycloalkyl, phenyl $C_1-C_6$ alkyl, an optionally substituted phenyl ring or $NR_{10}R_{11}$ wherein $R_{10}$ and $R_{11}$ are, each independently, hydrogen or $C_1-C_6$ alkyl; and $R_3$ is hydrogen, $C_1-C_6$ alkyl or an optionally substituted phenyl ring; or (b) $R_1$ and $R_3$, combined together, form a 5–8 membered, optionally substituted, carbomonocyclic ring, and $R_2$ is hydrogen, $C_1-C_4$ alkyl or $C_3-C_7$ cycloalkyl; $R_4$ is hydrogen, $C_1-C_6$ alkyl, $C_3-C_7$ cycloalkyl or phenyl $C_1-C_6$ alkyl; X is hydrogen, $C_1-C_6$ alkyl, $C_3-C_7$ cycloalkyl, $C_1-C_6$ alkoxy, $C_3-C_7$ cycloalkoxy, $C_1-C_6$ alkanoyloxy, benzoyloxy, amino, hydroxy, nitro, halogen or it is a methylenedioxy group linked to the positions 10 and 11 of the molecule, and the pharmaceutically acceptable salts thereof. The compounds according to the invention are useful in therapy as antitumor agents.

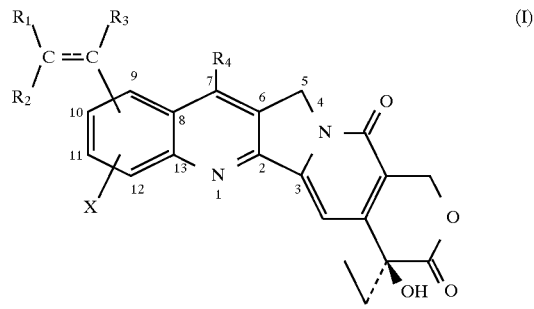

(I)

13 Claims, No Drawings

SUBSTITUTED CAMPTOTHECIN DERIVATIVES AND PROCESS FOR THEIR PREPARATION

The present invention relates to new substituted camptothecin derivatives possessing antitumor activity, to a process for their preparation, and to pharmaceutical compositions containing them.

BACKGROUND OF THE INVENTION

Camptothecin and some of its analogs display potent antitumor activity by the inhibition of Topoisomerase I, that is an enzyme involved in some important cellular functions and cellular growth (see, for instance, Wani et al., J. Med. Chem. 1987, 30, 1774; Hsiang et al., Cancer Res. 1989, 49, 4385; Cancer Res. 1989, 49, 1465).

Anticancer activity of Camptothecin both in vitro and in vivo is significantly greater for the lactone versus the carboxylate form (as disclosed, for instance, by W. J. Slichenmyer et al., in "The Current Status of Camptothecin Analogues as Antitumor Agents", J. Natl. Cancer Inst. 1993, 85, 271–291, and reference therein), since a closed a-hydroxy lactone ring is an important structural requirement for both passive diffusion of drug into cancer cells, as well as for successful drug interaction with the pharmacological target. It has recently been pointed out that, in the presence of biologically relevant levels of human albumin, the biologically active form of camptothecin has a very short half-life (about 12 min.), and 2 hours after drug addition to human plasma, a percentage greater than 99% of the drug has converted to camptothecin carboxylate, the biologically inactive and potentially toxic form of the drug (see Burke, G. T.; Mi, Z. "The Structural Basis of Camptothecin Interactions with Human Serum Albumin: Impact on Drug Stability", J. Med. Chem. 1994, 37, 40–46). The same authors disclose also the importance of the substitution in 9 and 7 positions on the camptothecin nucleus in order to improve drug stability in the presence of albumin.

There is therefore a need to find new camptothecin derivatives that have high intrinsic potency, and may gain, at the same time, stability in the presence of serum albumin.

DESCRIPTION OF THE INVENTION

Accordingly, the present invention relates to substituted camptothecin derivatives of formula (I)

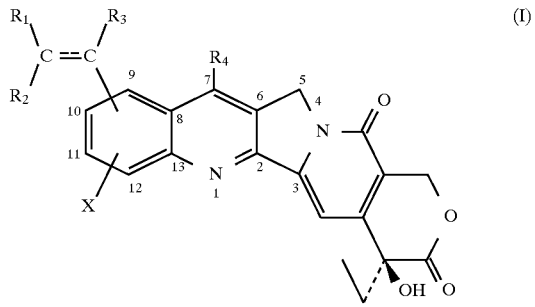

wherein
the symbol - - - - represents a single or double bond;
$R_1$, $R_2$ and $R_3$ are as defined under (a) or (b) below:
(a) $R_1$ and $R_2$ are, each independently,
hydrogen;
$C_1$–$C_4$ alkyl;
$C_3$–$C_7$ cycloalkyl;
phenyl $C_1$–$C_6$ alkyl;
an optionally substituted phenyl ring;
—$NR_5R_6$ wherein one of $R_5$ and $R_6$ is hydrogen, $C_1$–$C_6$ alkyl or benzyl and the other is hydrogen $C_1$–$C_6$ alkanoyl, an optionally substituted $C_1$–$C_6$ alkoxycarbonyl, an optionally substituted benzoyl, phenyl $C_1$–$C_6$ alkanoyl, an optionally substituted phenoxycarbonyl or phenyl $C_1$–$C_6$ alkoxycarbonyl, or $R_5$ and $R_6$, combined together with the nitrogen atom to which they are linked, form a 4–7 membered saturated, optionally substituted, heteromonocyclic ring residue, represented by a group (G)

wherein W is —C=O, $R_7$ is hydrogen or $C_1$–$C_6$ alkyl and n is an integer of 2 to 5;
$COOR_8$ wherein $R_8$ is hydrogen, $C_1$–$C_6$ alkyl, $C_3$–$C_7$ cycloalkyl or phenyl $C_1$–$C_6$ alkyl; or
$COR_9$ wherein $R_9$ is $C_1$–$C_6$ alkyl, $C_3$–$C_7$ cycloalkyl, phenyl $C_1$–$C_6$ alkyl, an optionally substituted phenyl ring or $NR_{10}R_{11}$ wherein $R_{10}$ and $R_{11}$ are, each independently, hydrogen or $C_1$–$C_6$ alkyl; and
$R_3$ is hydrogen, $C_1$–$C_6$ alkyl or an optionally substituted phenyl ring; or
(b) $R_1$ and $R_3$, combined together, form a 5–8 membered, optionally substituted, carbomonocyclic ring; and
$R_2$ is hydrogen, $C_1$–$C_4$ alkyl or $C_3$–$C_7$ cycloalkyl;
$R_4$ is hydrogen, $C_1$–$C_6$ alkyl, $C_3$–$C_7$ cycloalkyl or phenyl $C_1$–$C_6$ alkyl;
X is hydrogen, $C_1$–$C_6$ alkyl, $C_3$–$C_7$ cycloalkyl, $C_1$–$C_6$ alkoxy, $C_3$–$C_7$ cycloalkoxy, $C_1$–$C_6$ alkanoyloxy, benzoyloxy, amino, hydroxy, nitro, halogen or it is a methylenedioxy group linked to the positions 10 and 11 of the molecule, and the pharmaceutically acceptable salts thereof.

In the formulae of the present specification, a dotted line (- - -) indicates a substituent below the plane of the ring; a wedged line (—◂) indicates a substituent above the plane of the ring.

When in a compound of formula (I) the symbol - - - - means a double bond, both Z and E isomers and a mixture of Z and E isomers are included into the scope of the present invention. Pharmaceutically acceptable salts according the invention are the salts with pharmaceutically acceptable acids, both inorganic acids such as, e.g. hydrochloric, sulfuric, phosphoric, diphosphoric, hydrobromic or nitric acid, and organic acids such as, e.g., citric, fumaric, maleic, malic, ascorbic, succinic, tartaric, benzoic, acetic, methanesulfonic, ethanesulfonic, benzenesulfonic, or p-toluensulfonic acid.

Pharmaceutically acceptable salts of the compounds of formula (I) containing an acidic, i.e. carboxy, group with pharmaceutically acceptable bases are also included in the scope of the present invention.

Pharmaceutically acceptable bases may be both inorganic bases such as, for instance, alkali metal, e.g. sodium or potassium, or alkaline earth metal, e.g. calcium or magnesium, hydroxides, and organic bases such as, for instance, alkyl amines, e.g. methylamine or triethylamine, aralkylamines, e.g. benzylamine, dibenzylamine, a- or b-phenyl-ethylamine, or heterocyclic amines such as, e.g., piperidine, 1-methylpiperidine, piperazine or morpholine.

An optionally substituted phenyl ring may be represented by a group

wherein
Q, linked to the ortho, meta or para position of the phenyl ring, represents hydrogen, $C_1$–$C_6$ alkyl, $C_1$–$C_6$ alkoxy, $C_1$–$C_6$, alkanoyloxy, nitro or halogen.

Preferably Q is hydrogen, $C_1$–$C_4$ alkyl, $C_1$–$C_4$ alkoxy or halogen.

Particularly preferred values of Q are hydrogen, methoxy and chlorine.

An optionally substituted benzoyl may be represented by a group

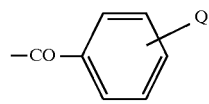

wherein Q is as defined above.

An optionally substituted phenoxycarbonyl may be represented by a group

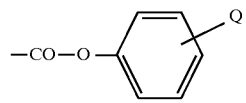

wherein Q is as defined above.

A 5–8 membered, optionally substituted carbomonocyclic ring is, when the symbol - - - - is used to denote a single bond, for example cyclopentyl or cyclohexyl, or, when the symbol - - - - is used to denote a double bond, cyclopenten-1-yl or cyclohexen-1-yl.

In the present specification, the hydrocarbon chain of the alkyl, alkoxy, alkanoyl, alkanoyloxy and alkoxycarbonyl groups may be a straight or branched chain.

Preferably, $C_1$–$C_6$ alkyl is $C_1$–$C_4$ alkyl, e.g. methyl, ethyl, n-propyl, isopropyl, n-butyl, sec-butyl or t-butyl.

Preferably, $C_1$–$C_4$ alkyl is methyl, ethyl or propyl.

Preferably, $C_3$–$C_7$, cycloalkyl is $C_4$–$C_6$ cycloalkyl, e.g. cyclobutyl, cyclopentyl or cyclohexyl.

Preferably, $C_1$–$C_6$ alkoxy is $C_1$–$C_4$ alkoxy, e.g. methoxy, ethoxy or propoxy.

Preferably, $C_1$–$C_6$ alkanoyl is $C_1$–$C_4$ alkanoyl, e.g. methanoyl, ethanoyl or propanoyl.

Preferably, $C_1$–$C_6$ alkanoyloxy is $C_1$–$C_4$ alkanoyloxy, e.g. methanoyloxy, ethanoyloxy or propanoyloxy.

Preferably, $C_1$–$C_6$ alkoxycarbonyl is $C_1$–$C_4$ alkoxycarbonyl, e.g. methoxycarbonyl, ethoxycarbonyl, n-propoxycarbonyl or isopropoxicarbonyl.

Preferably, an optionally substituted $C_1$–$C_6$ alkoxycarbonyl is trichloroethoxycarbonyl.

Preferred meanings of the heteromonocyclic ring residue represented by the above defined group (G) are

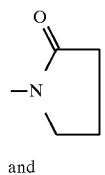

and

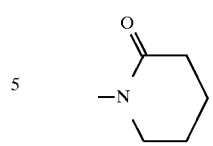

A preferred class of compounds according to this invention is represented by compounds of the above formula (I) wherein the symbol - - - - represents a single or double bond; $R_1$ and $R_2$ are, each independently, hydrogen;
—$NR_5R_6$ wherein one of $R_5$ and $R_6$ is hydrogen and the other is hydrogen, $C_1$–$C_6$ alkanoyl, an optionally substituted benzoyl, phenyl $C_1$–$C_6$ alkanoyl, $C_1$–$C_6$ alkoxycarbonyl, phenoxy-carbonyl or phenyl $C_1$–$C_6$ alkoxycarbonyl;
$COOR_8$ wherein $R_8$ is hydrogen or $C_1$–$C_6$ alkyl; or
$COR_9$ wherein $R_9$ is $C_1$–$C_6$ alkyl, unsubstituted phenyl or $NR_{10}R_{11}$ wherein $R_{10}$ and $R_{11}$ are both hydrogen;
$R_3$ is hydrogen;
$R_4$ is hydrogen or $C_1$–$C_6$ alkyl;
X is hydrogen, hydroxy, amino, $C_1$–$C_6$ alkoxy or it is a methylenedioxy group linked to the positions 10 and 11 of the molecule, and the pharmaceutically acceptable salts thereof.

Examples of specific compounds preferred under the invention are the following:
9-vinyl camptothecin (1);
(E)-9-(2-methoxycarbonyl-ethenyl)camptothecin (2);
9-(2-hydroxycarbonyl-ethenyl)camptothecin (3);
(Z)-9-(2-acetylamino-2-methoxycarbonyl-ethenyl) camptothecin (4);
9-(2-acetylamino-2-hydroxycarbonyl-ethenyl)camptothecin (5);
9-(3-oxo-but-1-enyl)camptothecin (6);
9-(3-oxo-3-phenyl-propenyl)camptothecin (7);
9-(2-aminocarbonyl-ethenyl)camptothecin (8);
7-ethyl-9-vinyl camptothecin (9);
7-ethyl-9-(2-methoxycarbonyl-ethenyl)camptothecin (10);
7-ethyl-9-(2-hydroxycarbonyl-ethenyl)camptothecin (11);
7-ethyl-9-(2-acetylamino-2-methoxycarbonyl-ethenyl) camptothecin (12);
7-ethyl-9-(2-acetylamino-2-hydroxycarbonyl-ethenyl) camptothecin (13);
7-ethyl-9-(3-oxo-but-1-enyl)camptothecin (14);
7-ethyl-9-(3-oxo-3-phenyl-propenyl)camptothecin (15);
7-ethyl-9-(2-aminocarbonyl-ethenyl)camptothecin (16);
10-vinyl camptothecin (17);
(E) 10-(2-methoxycarbonyl-ethenyl)camptothecin (18);
10-(2-hydroxycarbonyl-ethenyl)camptothecin (19);
10-(2-acetylamino-2-methoxycarbonyl-ethenyl) camptothecin (20);
10-(2-acetylamino-2-hydroxycarbonyl-ethenyl) camptothecin (21);
10-(3-oxo-but-1-enyl)camptothecin (22);
10-(3-oxo-3-phenyl-propenyl)camptothecin (23);
10-(2-aminocarbonyl-ethenyl)camptothecin (24);
7-ethyl-10-vinyl camptothecin (25);
7-ethyl-10-(2-methoxycarbonyl-ethenyl)camptothecin (26);
7-ethyl-10-(2-hydroxycarbonyl-ethenyl)camptothecin (27);
7-ethyl-10-(2-acetylamino-2-methoxycarbonyl-ethenyl) camptothecin (28);
7-ethyl-10-(2-acetylamino-2-hydroxycarbonyl-ethenyl) camptothecin (29);
7-ethyl-10-(3-oxo-but-1-enyl)camptothecin (30);

7-ethyl-10-(3-oxo-3-phenyl-propenyl)camptothecin (31);
7-ethyl-10-(2-aminocarbonyl-ethenyl)camptothecin (32);
10-hydroxy-9-vinyl camptothecin (33);
10-hydroxy-9-(2-methoxycarbonyl-ethenyl)camptothecin (34);
10-hydroxy-9-(2-hydroxycarbonyl-ethenyl)camptothecin (35);
10-hydroxy-9-(2-acetylamino-2-methoxycarbonyl-ethenyl) camptothecin (36);
10-hydroxy-9-(2-acetylamino-2-hydroxycarbonyl-ethenyl) camptothecin (37);
10-hydroxy-9-(3-oxo-but-1-enyl)camptothecin (38);
10-hydroxy-9-(3-oxo-3-phenyl-propenyl)camptothecin (39);
10-hydroxy-9-(2-aminocarbonyl-ethenyl)camptothecin (40);
10,11-methylendioxy-9-vinyl camptothecin (41);
10,11-methylendioxy-9-(2-methoxycarbonyl-ethenyl) camptothecin (42);
10,11-methylendioxy-9-(2-hydroxycarbonyl-ethenyl) camptothecin (43);
10,11-methylendioxy-9-(2-acetylamino-2-methoxycarbonyl-ethenyl)camptothecin (44);
10,11-methylendioxy-9-(2-acetylamino-2-hydroxycarbonyl-ethenyl)camptothecin (45);
10,11-methylendioxy-9-(3-oxo-but-1-enyl)camptothecin (46);
10,11-methylendioxy-9-(3-oxo-3-phenyl-propenyl) camptothecin (47);
10,11-methylendioxy-9-(2-aminocarbonyl-ethenyl) camptothecin (48);
10-methoxy-9-vinyl camptothecin (49);
10-methoxy-9-(2-methoxycarbonyl-ethenyl)camptothecin (50);
10-methoxy-9-(2-hydroxycarbonyl-ethenyl)camptothecin (51);
10-methoxy-9-(2-acetylamino-2-methoxycarbonyl-ethenyl) camptothecin (52);
10-methoxy-9-(2-acetylamino-2-hydroxycarbonyl-ethenyl) camptothecin (53);
10-methoxy-9-(3-oxo-but-1-enyl)camptothecin (54);
10-methoxy-9-(3-oxo-3-phenyl-propenyl)camptothecin (55);
10-methoxy-9-(2-aminocarbonyl-ethenyl)camptothecin (56);
11-vinyl camptothecin (57);
11-(2-methoxycarbonyl-ethenyl)camptothecin (58);
11-(2-hydroxycarbonyl-ethenyl)camptothecin (59);
11-(2-acetylamino-2-methoxycarbonyl-ethenyl) camptothecin (60);
11-(2-acetylamino-2-hydroxycarbonyl-ethenyl) camptothecin (61);
11-(3-oxo-but-1-enyl)camptothecin (62);
11-(3-oxo-3-phenyl-propenyl)camptothecin (63);
11-(2-aminocarbonyl-ethenyl)camptothecin (64);
12-vinyl camptothecin (65);
(E)-12-(2-methoxycarbonyl-ethenyl)camptothecin (66);
12-(2-hydroxycarbonyl-ethenyl)camptothecin (67);
(Z)-12-(2-acetylamino-2-methoxycarbonyl-ethenyl) camptothecin (68);
12-(2-acetylamino-2-hydroxycarbonyl-ethenyl) camptothecin (69);
12-(3-oxo-but-1-enyl)camptothecin (70);
12-(3-oxo-3-phenyl-propenyl)camptothecin (71);
12-(2-aminocarbonyl-ethenyl)camptothecin (72);
9-amino-10-vinyl camptothecin (73);
9-amino-10-(2-methoxycarbonyl-ethenyl)camptothecin (74);
9-amino-10-(2-hydroxycarbonyl-ethenyl)camptothecin (75);
9-amino-10-(2-acetylamino-2-methoxycarbonyl-ethenyl) camptothecin (76);
9-amino-10-(2-acetylamino-2-hydroxycarbonyl-ethenyl) camptothecin (77);
9-amino-10-(3-oxo-but-1-enyl)camptothecin (78);
9-amino-10-(3-oxo-3-phenyl-propenyl)camptothecin (79);
9-amino-10-(2-aminocarbonyl-ethenyl)camptothecin (80);
7-ethyl-9-amino-10-vinyl camptothecin (81);
7-ethyl-9-amino-10-(2-methoxycarbonyl-ethenyl) camptothecin (82);
7-ethyl-9-amino-10-(2-hydroxycarbonyl-ethenyl) camptothecin (83);
7-ethyl-9-amino-10-(2-acetylamino-2-methoxycarbonyl-ethenyl)camptothecin (84);
7-ethyl-9-amino-10-(2-acetylamino-2-hydroxycarbonyl-ethenyl)camptothecin (85);
7-ethyl-9-amino-10-(3-oxo-but-1-enyl)camptothecin (86);
7-ethyl-9-amino-10-(3-oxo-3-phenyl-propenyl) camptothecin (87);
7-ethyl-9-amino-10-(2-aminocarbonyl-ethenyl) camptothecin (88);
9-ethyl camptothecin (1');
9-(2-methoxycarbonyl-ethyl)camptothecin (2');
9-(2-hydroxycarbonyl-ethyl)camptothecin (3');
9-[(2-acetylamino-2-ethoxycarbonyl]-ethyl)camptothecin (4');
9-[(2-amino-2-methoxycarbonyl]-ethyl)camptothecin (5');
9-[(2-amino-2-hydroxycarbonyl)-ethyl]camptothecin (6');
9-[(2-acetylamino-2-hydroxycarbony))-ethyl]camptothecin (7');
9-(3-oxo-butyl)camptothecin (8');
9-(3-oxo-3-phenyl-propyl)camptothecin (9');
9-(2-aminocarbonyl-ethyl)camptothecin (10');
7-ethyl-9-ethyl camptothecin (11');
7-ethyl-9-(2-methoxycarbonyl-ethyl)camptothecin (12');
7-ethyl-9-(2-hydroxycarbonyl-ethyl)camptothecin (13');
7-ethyl-9-[(2-acetylamino-2-methoxycarbonyl]-ethyl) camptothecin (14');
7-ethyl-9-[(2-amino-2-methoxycarbonyl]-ethyl) camptothecin (15');
7-ethyl-9-[(2-amino-2-hydroxycarbonyl)-ethyl] camptothecin (16');
7-ethyl-9-[(2-acetylamino-2-hydroxycarbonyl)-ethyl] camptothecin (17');
7-ethyl-9-(3-oxo-butyl)camtiptothecin (18');
7-ethyl-9-(3-oxo-3-phenyl-propyl)camptothecin (19');
7-ethyl-9-(2-aminocarbonyl-ethyl)camptothecin (20');
10-ethyl camptothecin (21');
10-(2-methoxycarbonyl-ethyl)camptothecin (22');
10-(2-hydroxycarbonyl-ethyl)camptothecin (23');
10-[(2-acetylamino-2-methoxycarbonyl]-ethyl) camptothecin (24');
10-[(2-amino-2-methoxycarbonyl]-ethyl)camptothecin (25');
10-[(2-amino-2-hydroxycarbonyl)-ethyl]camptothecin (26');
10-[(2-acetylamino-2-hydroxycarbony)-ethyl]camptothecin (27');
10-(3-oxo-butyl)camptothecin (28');
10-(3-oxo-3-phenyl-propyl)camptothecin (29');
10-(2-aminocarbonyl-ethyl)camptothecin (30');
7-ethyl-10-ethyl camptothecin (31');
7-ethyl-10-(2-methoxycarbonyl-ethyl)camptothecin (32');
7-ethyl-10-(2-hydroxycarbonyl-ethyl)camptothecin (33');
7-ethyl-10-[(2-acetylamino-2-methoxycarbonyl]-ethyl) camptothecin (34');

7-ethyl-10-[(2-amino-2-methoxycarbonyl)-ethyl) camptothecin (35');
7-ethyl-10-[(2-amino-2-hydroxycarbonyl)-ethyl] camptothecin (36');
7-ethyl-10-[(2-acetylamino-2-hydroxycarbony)-ethyl] camptothecin (37');
7-ethyl-10-(3-oxo-butyl)camptothecin (38');
7-ethyl-10-(3-oxo-3-phenyl-propyl)camptothecin (39');
7-ethyl-10-(2-aminocarbonyl-ethyl)camptothecin (40');
11-ethyl camptothecin (41');
11-(2-methoxycarbonyl-ethyl)camptothecin (42');
11-(2-hydroxycarbonyl-ethyl)camptothecin (43');
11-[(2-acetylamino-2-methoxycarbonyl]-ethyl) camptothecin (44');
11-[(2-amino-2-methoxycarbonyl)-ethyl)camptothecin (45');
11-[(2-amino-2-hydroxycarbonyl)-ethyl]camptothecin (46');
11-[(2-acetylamino-2-hydroxycarbonyl)-ethyl] camptothecin (47');
11-(3-oxo-butyl)camptothecin (48');
11-(3-oxo-3-phenyl-propyl)camptothecin (49');
11-(2-aminocarbonyl-ethyl)camptothecin (50');
9-amino-12-ethyl camptothecin (51');
9-amino-12-(2-methoxycarbonyl-ethyl)camptothecin (52');
9-amino-12-(2-hydroxycarbonyl-ethyl)camptothecin (53');
9-amino-12-[(2-acetylamino-2-methoxycarbonyl]-ethyl) camptothecin (54');
9-amino-12-[(2-amino-2-methoxycarbonyl]-ethyl) camptothecin (55');
9-amino-12-[(2-amino-2-hydroxycarbonyl)-ethyl] camptothecin (56');
9-amino-12-[(2-acetylamino-2-hydroxycarbonyl)-ethyl] camptothecin (57');
9-amino-12-(3-oxo-butyl)camptothecin (58');
9-amino-12-(3-oxo-3-phenyl-propyl)camptothecin (59');
9-amino-12-(2-aminocarbonyl-ethyl)camptothecin (60');
10-amino-9-ethyl camptothecin (61');
10-amino-9-(2-methoxycarbonyl-ethyl)camptothecin (62');
10-amino-9-(2-hydroxycarbonyl-ethyl)camptothecin (63');
10-amino-9-[(2-acetylamino-2-methoxycarbonyl]-ethyl] camptothecin (64');
10-amino-9-[(2-amino-2-methoxycarbonyl]-ethyl) camptothecin (65');
10-amino-9-[(2-amino-2-hydroxycarbonyl)-ethyl] camptothecin (66');
10-amino-9-[(2-acetylamino-2-hydroxycarbony)-ethyl] camptothecin (67');
10-amino-9-(3-oxo-butyl)camptothecin (68');
10-amino-9-(3-oxo-3-phenyl-3-one-propyl)camptothecin (69');
10-amino-9-(2-aminocarbonyl-ethyl)camptothecin (70');
12-ethyl camptothecin (71');
12-(2-methoxycarbonyl-ethyl)camptothecin (72');
12-(2-hydroxycarbonyl-ethyl)camptothecin (73');
12-[(2R,S,)(2-acetylamino-2-methoxycarbonyl]-ethyl] camptothecin (74');
12-[(2-amino-2-methoxycarbonyl)-ethyl)camptothecin (75');
12-[(2-amino-2-hydroxycarbonyl)-ethyl]camptothecin (76');
12-[(2-acetylamino-2-hydroxycarbony)-ethyl]camptothecin (77');
12-(3-oxo-butyl)camptothecin (78');
12-(3-oxo-3-phenyl-propyl)camptothecin (79');
12-(2-aminocarbonyl-ethyl)camptothecin (80');
10-hydroxy-9-ethyl camptothecin (81');
10-hydroxy-9-(2-methoxycarbonyl-ethyl)camptothecin (82');
10-hydroxy-9-(2-hydroxycarbonyl-ethyl)camptothecin (83');
10-hydroxy-9-[(2-acetylamino-2-methoxycarbonyl]-ethyl) camptothecin (84');
10-hydroxy-9-[(2-amino-2-methoxycarbonyl]-ethyl) camptothecin (85');
10-hydroxy-9-[(2-amino-2-hydroxycarbonyl)-ethyl] camptothecin (86');
10-hydroxy-9-[(2-acetylamino-2-hydroxycarbony)-ethyl] camptothecin (87');
10-hydroxy-9-(3-oxo-butyl)camptothecin (88');
10-hydroxy-9-(3-oxo-3-phenyl-3-one-propyl)camptothecin (89');
10-hydroxy-9-(2-aminocarbonyl-ethyl)camptothecin (90');
10,11-methylendioxy-9-ethyl camptothecin (91');
10,11-methylendioxy-9-(2-methoxycarbonyl-ethyl) camptothecin (92');
10,11-methylendioxy-9-(2-hydroxycarbonyl-ethyl) camptothecin (93');
10,11-methylendioxy-9-[(2-acetylamino-2-methoxycarbonyl]ethyl)camptothecin (94');
10,11-methylendioxy-9-[(2-amino-2-methoxycarbonyl]-ethyl)camptothecin (95');
10,11-methylendioxy-9-[(2-amino-2-hydroxycarbonyl)-ethyl]camptothecin (96');
10,11-methylendioxy-9-[(2-acetylamino-2-hydroxycarbony)-ethyl]camptothecin (97');
10,11-methylendioxy-9-(3-oxo-butyl)camptothecin (98');
10,11-methylendioxy-9-(3-oxo-3-phenyl-propyl) camptothecin (99');
10,11-methylendioxy-9-(2-aminocarbonyl-ethyl) camptothecin (100');
10-methoxy-9-ethyl camptothecin (101');
10-methoxy-9-(2-methoxycarbonyl-ethyl)camptothecin (102');
10-methoxy-9-(2-hydroxycarbonyl-ethyl)camptothecin (103');
10-methoxy-9-[(2-acetylamino-2-methoxycarbonyl]-ethyl) camptothecin (104');
10-methoxy-9-[(2-amino-2-methoxycarbonyl]-ethyl) camptothecin (105');
10-methoxy-9-[(2-amino-2-hydroxycarbonyl)-ethyl] camptothecin (106');
10-methoxy-9-[(2-acetylamino-2-hydroxycarbony)-ethyl] camptothecin (107');
10-methoxy-9-(3-oxo-butyl)camptothecin (108');
10-methoxy-9-(3-oxo-3-phenyl-propyl)camptothecin (109');
10-methoxy-9-(2-aminocarbonyl-ethyl)camptothecin (110');
and, where a salifiable substituent is present on the molecule framework, their pharmaceutically acceptable salts.

The structural formula of the above listed compounds is illustrated in the following Table 1 with reference to the above formula (I) wherein the symbol ---- represents a double bond, and Table 2 with reference to the above formula (I) wherein the symbol ---- represents a single bond.

TABLE 1

| Compound | | $R_5$ | $R_6$ | $R_8$ | $R_9$ | $R_4$ | X |
|---|---|---|---|---|---|---|---|
| | 9-substituent | | | | | | |
| 1 | $-CH=CH_2$ | — | — | — | — | H | H |
| 2 | $-CH=CH-COOR_8$ | — | — | $CH_3$ | — | H | H |
| 3 | $-CH=CH-COOR_8$ | — | — | H | — | H | H |
| 4 | $-CH=C-COOR_8$ $\|$ $NR_5R_6$ | H | $COCH_3$ | $CH_3$ | — | H | H |
| 5 | $-CH=C-COOR_8$ $\|$ $NR_5R_6$ | H | $COCH_3$ | H | — | H | H |
| 6 | $-CH=CH-COR_9$ | — | — | — | $CH_3$ | H | H |
| 7 | $-CH=CH-COR_9$ | — | — | — | Ph | H | H |
| 8 | $-CH=CH-COR_9$ | — | — | — | $NH_2$ | H | H |
| 9 | $-CH=CH_2$ | — | — | — | — | Et | H |
| 10 | $-CH=CH-COOR_8$ | — | — | $CH_3$ | — | Et | H |
| 11 | $-CH=CH-COOR_8$ | — | — | H | — | Et | H |
| 12 | $-CH=C-COOR_8$ $\|$ $NR_5R_6$ | H | $COCH_3$ | $CH_3$ | — | Et | H |
| 13 | $-CH=C-COOR_8$ $\|$ $NR_5R_6$ | H | $COCH_3$ | H | — | Et | H |
| 14 | $-CH=CH-COR_9$ | — | — | — | $CH_3$ | Et | H |
| 15 | $-CH=CH-COR_9$ | — | — | — | Ph | Et | H |
| 16 | $-CH=CH-COR_9$ | — | — | — | $NH_2$ | Et | H |
| | 10-substituent | | | | | | |
| 17 | $-CH=CH_2$ | — | — | — | — | H | H |
| 18 | $-CH=CH-COOR_8$ | — | — | $CH_3$ | — | H | H |
| 19 | $-CH=CH-COOR_8$ | — | — | H | — | H | H |
| 20 | $-CH=C-COOR_8$ $\|$ $NR_5R_6$ | H | $COCH_3$ | $CH_3$ | — | H | H |
| 21 | $-CH=C-COOR_8$ $\|$ $NR_5R_6$ | H | $COCH_3$ | H | — | H | H |
| 22 | $-CH=CH-COR_9$ | — | — | — | $CH_3$ | H | H |
| 23 | $-CH=CH-COR_9$ | — | — | — | Ph | H | H |
| 24 | $-CH=CH-COR_9$ | — | — | — | $NH_2$ | H | H |
| 25 | $-CH=CH_2$ | — | — | — | — | Et | H |
| 26 | $-CH=CH-COOR_8$ | — | — | $CH_3$ | — | Et | H |
| 27 | $-CH=CH-COOR_8$ | — | — | H | — | Et | H |
| 28 | $-CH=C-COOR_8$ $\|$ $NR_5R_6$ | H | $COCH_3$ | $CH_3$ | — | Et | H |
| 29 | $-CH=C-COOR_8$ $\|$ $NR_5R_6$ | H | $COCH_3$ | H | — | Et | H |
| 30 | $-CH=CH-COR_9$ | — | — | — | $CH_3$ | Et | H |
| 31 | $-CH=CH-COR_9$ | — | — | — | Ph | Et | H |
| 32 | $-CH=CH-COR_9$ | — | — | — | $NH_2$ | Et | H |
| | 9-substituent | | | | | | |
| 33 | $-CH=CH_2$ | — | — | — | — | H | 10-OH |
| 34 | $-CH=CH-COOR_8$ | — | — | $CH_3$ | — | H | 10-OH |
| 35 | $-CH=CH-COOR_8$ | — | — | H | — | H | 10-OH |
| 36 | $-CH=C-COOR_8$ $\|$ $NR_5R_6$ | H | $COCH_3$ | $CH_3$ | — | H | 10-OH |
| 37 | $-CH=C-COOR_8$ $\|$ $NR_5R_6$ | H | $COCH_3$ | H | — | H | 10-OH |
| 38 | $-CH=CH-COR_9$ | — | — | — | $CH_3$ | H | 10-OH |

TABLE 1-continued

| Compound | $R_5$ | $R_6$ | $R_8$ | $R_9$ | $R_4$ | X |
|---|---|---|---|---|---|---|
| 39 | —CH=CH—COR$_9$ | — | — | — | Ph | H | 10-OH |
| 40 | —CH=CH—COR$_9$ | — | — | — | NH$_2$ | H | 10-OH |
| 41 | —CH=CH$_2$ | — | — | — | — | H | 10,11-OCH$_2$O— |
| 42 | —CH=CH—COOR$_8$ | — | — | CH$_3$ | — | H | 10,11-OCH$_2$O— |
| 43 | —CH=CH—COOR$_8$ | — | — | H | — | H | 10,11-OCH$_2$O— |
| 44 | —CH=C(NR$_5$R$_6$)—COOR$_8$ | H | COCH$_3$ | CH$_3$ | — | H | 10,11-OCH$_2$O— |
| 45 | —CH=C(NR$_5$R$_6$)—COOR$_8$ | H | COCH$_3$ | H | — | H | 10,11-OCH$_2$O— |
| 46 | —CH=CH—COR$_9$ | — | — | — | CH$_3$ | H | 10,11-OCH$_2$O— |
| 47 | —CH=CH—COR$_9$ | — | — | — | Ph | H | 10,11-OCH$_2$O— |
| 48 | —CH=CH—COR$_9$ | — | — | — | NH$_2$ | H | 10,11-OCH$_2$O— |
| 49 | —CH=CH$_2$ | — | — | — | — | H | 10-OCH$_3$ |
| 50 | —CH=CH—COOR$_8$ | — | — | CH$_3$ | — | H | 10-OCH$_3$ |
| 51 | —CH=CH—COOR$_8$ | — | — | H | — | H | 10-OCH$_3$ |
| 52 | —CH=C(NR$_5$R$_6$)—COOR$_8$ | H | COCH$_3$ | CH$_3$ | — | H | 10-OCH$_3$ |
| 53 | —CH=C(NR$_5$R$_6$)—COOR$_8$ | H | COCH$_3$ | H | — | H | 10-OCH$_3$ |
| 54 | —CH=CH—COR$_9$ | — | — | — | CH$_3$ | H | 10-OCH$_3$ |
| 55 | —CH=CH—COR$_9$ | — | — | — | Ph | H | 10-OCH$_3$ |
| 56 | —CH=CH—COR$_9$ | — | — | — | NH$_2$ | H | 10-OCH$_3$ |

11-substituted

| Compound | $R_5$ | $R_6$ | $R_8$ | $R_9$ | $R_4$ | X |
|---|---|---|---|---|---|---|
| 57 | —CH=CH$_2$ | — | — | — | — | H | H |
| 58 | —CH=CH—COOR$_8$ | — | — | CH$_3$ | — | H | H |
| 59 | —CH=CH—COOR$_8$ | — | — | H | — | H | H |
| 60 | —CH=C(NR$_5$R$_6$)—COOR$_8$ | H | COCH$_3$ | CH$_3$ | — | H | H |
| 61 | —CH=C(NR$_5$R$_6$)—COOR$_8$ | H | COCH$_3$ | H | — | H | H |
| 62 | —CH=CH—COR$_9$ | — | — | — | CH$_3$ | H | H |
| 63 | —CH=CH—COR$_9$ | — | — | — | Ph | H | H |
| 64 | —CH=CH—COR$_9$ | — | — | — | NH$_2$ | H | H |

12-substituent

| Compound | $R_5$ | $R_6$ | $R_8$ | $R_9$ | $R_4$ | X |
|---|---|---|---|---|---|---|
| 65 | —CH=CH$_2$ | — | — | — | — | H | H |
| 66 | —CH=CH—COOR$_8$ | — | — | CH$_3$ | — | H | H |
| 67 | —CH=CH—COOR$_8$ | — | — | H | — | H | H |
| 68 | —CH=C(NR$_5$R$_6$)—COOR$_8$ | H | COCH$_3$ | CH$_3$ | — | H | H |
| 69 | —CH=C(NR$_5$R$_6$)—COOR$_8$ | H | COCH$_3$ | H | — | H | H |
| 70 | —CH=CH—COR$_9$ | — | — | — | CH$_3$ | H | H |
| 71 | —CH=CH—COR$_9$ | — | — | — | Ph | H | H |
| 72 | —CH=CH—COR$_9$ | — | — | — | NH$_2$ | H | H |

10-substituent

| Compound | $R_5$ | $R_6$ | $R_8$ | $R_9$ | $R_4$ | X |
|---|---|---|---|---|---|---|
| 73 | —CH=CH$_2$ | — | — | — | — | H | 9-NH$_2$ |
| 74 | —CH=CH—COOR$_8$ | — | — | CH$_3$ | — | H | 9-NH$_2$ |
| 75 | —CH=CH—COOR$_8$ | — | — | H | — | H | 9-NH$_2$ |
| 76 | —CH=C(NR$_5$R$_6$)—COOR$_8$ | H | COCH$_3$ | CH$_3$ | — | H | 9-NH$_2$ |
| 77 | —CH=C(NR$_5$R$_6$)—COOR$_8$ | H | COCH$_3$ | H | — | H | 9-NH$_2$ |

TABLE 1-continued

| Compound | R₅ | R₆ | R₈ | R₉ | R₄ | X |
|---|---|---|---|---|---|---|
| 78 | —CH=CH—COR₉ | — | — | — | CH₃ | H | 9-NH₂ |
| 79 | —CH=CH—COR₉ | — | — | — | Ph | H | 9-NH₂ |
| 80 | —CH=CH—COR₉ | — | — | — | NH₂ | H | 9-NH₂ |
| 81 | —CH=CH₂ | — | — | — | — | Et | 9-NH₂ |
| 82 | —CH=CH—COOR₈ | — | — | CH₃ | — | Et | 9-NH₂ |
| 83 | —CH=CH—COOR₈ | — | — | H | — | Et | 9-NH₂ |
| 84 | —CH=C(NR₅R₆)—COOR₈ | H | COCH₃ | CH₃ | — | Et | 9-NH₂ |
| 85 | —CH=C(NR₅R₆)—COOR₈ | H | COCH₃ | H | — | Et | 9-NH₂ |
| 86 | —CH=CH—COR₉ | — | — | — | CH₃ | Et | 9-NH₂ |
| 87 | —CH=CH—COR₉ | — | — | — | Ph | Et | 9-NH₂ |
| 88 | —CH=CH—COR₉ | — | — | — | NH₂ | Et | 9-NH₂ |

Note: columns shown as R₅ | R₆ | R₈ | R₉ | R₄ | X. For compounds 82-85 the table places CH₃/H under R₈ and — under R₉.

TABLE 2

| Compound | R₅ | R₆ | R₈ | R₉ | R₄ | X |
|---|---|---|---|---|---|---|
| 9-substituent | | | | | | |
| 1' | —CH₂—CH₃ | — | — | — | — | H | H |
| 2' | -(CH₂)₂—COOR₈ | — | — | CH₃ | — | H | H |
| 3' | -(CH₂)₂—COOR₈ | — | — | H | — | H | H |
| 4' | —CH₂—CH(NR₅R₆)—COOR₈ | H | COCH₃ | CH₃ | — | H | H |
| 5' | —CH₂—CH(NR₅R₆)—COOR₈ | H | H | CH₃ | — | H | H |
| 6' | —CH₂—CH(NR₅R₆)—COOR₈ | H | H | H | — | H | H |
| 7' | —CH₂—CH(NR₅R₆)—COOR₈ | H | COCH₃ | H | — | H | H |
| 8' | -(CH₂)₂—COR₉ | — | — | — | CH₃ | H | H |
| 9' | -(CH₂)₂—COR₉ | — | — | — | Ph | H | H |
| 10' | -(CH₂)₂—COR₉ | — | — | — | NH₂ | H | H |
| 11' | —CH₂—CH₃ | — | — | — | — | Et | H |
| 12' | -(CH₂)₂—COOR₈ | — | — | CH₃ | — | Et | H |
| 13' | -(CH₂)₂—COOR₈ | — | — | H | — | Et | H |
| 14' | —CH₂—CH(NR₅R₆)—COOR₈ | H | COCH₃ | CH₃ | — | Et | H |
| 15' | —CH₂—CH(NR₅R₆)—COOR₈ | H | H | CH₃ | — | Et | H |
| 16' | —CH₂—CH(NR₅R₆)—COOR₈ | H | H | H | — | Et | H |
| 17' | —CH₂—CH(NR₅R₆)—COOR₈ | H | COCH₃ | H | — | Et | H |
| 18' | -(CH₂)₂—COR₉ | — | — | — | CH₃ | Et | H |
| 19' | -(CH₂)₂—COR₉ | — | — | — | Ph | Et | H |
| 20' | -(CH₂)₂—COR₉ | — | — | — | NH₂ | Et | H |
| 10-substituent | | | | | | |
| 21' | —CH₂—CH₃ | — | — | — | — | H | H |
| 22' | -(CH₂)₂—COOR₈ | — | — | CH₃ | — | H | H |
| 23' | -(CH₂)₂—COOR₈ | — | — | H | — | H | H |

TABLE 2-continued

| Compound | | $R_5$ | $R_6$ | $R_8$ | $R_9$ | $R_4$ | X |
|---|---|---|---|---|---|---|---|
| 24' | —CH$_2$—CH(NR$_5$R$_6$)—COOR$_8$ | H | COCH$_3$ | CH$_3$ | — | H | H |
| 25' | —CH$_2$—CH(NR$_5$R$_6$)—COOR$_8$ | H | H | CH$_3$ | — | H | H |
| 26' | —CH$_2$—CH(NR$_5$R$_6$)—COOR$_8$ | H | H | H | — | H | H |
| 27' | —CH$_2$—CH(NR$_5$R$_6$)—COOR$_8$ | H | COCH$_3$ | H | — | H | H |
| 28' | -(CH$_2$)$_2$—COR$_9$ | — | — | — | CH$_3$ | H | H |
| 29' | -(CH$_2$)$_2$—COR$_9$ | — | — | — | Ph | H | H |
| 30' | -(CH$_2$)$_2$—COR$_9$ | — | — | — | NH$_2$ | H | H |
| 31' | —CH$_2$—CH$_3$ | — | — | — | — | Et | H |
| 32' | -(CH$_2$)$_2$—COOR$_8$ | — | — | CH$_3$ | — | Et | H |
| 33' | -(CH$_2$)$_2$—COOR$_8$ | — | — | H | — | Et | H |
| 34' | —CH$_2$—CH(NR$_5$R$_6$)—COOR$_8$ | H | COCH$_3$ | CH$_3$ | — | Et | H |
| 35' | —CH$_2$—CH(NR$_5$R$_6$)—COOR$_8$ | H | H | CH$_3$ | — | Et | H |
| 36' | —CH$_2$—CH(NR$_5$R$_6$)—COOR$_8$ | H | H | H | — | Et | H |
| 37' | —CH$_2$—CH(NR$_5$R$_6$)—COOR$_8$ | H | COCH$_3$ | H | — | Et | H |
| 38' | -(CH$_2$)$_2$—COR$_9$ | — | — | — | CH$_3$ | Et | H |
| 39' | -(CH$_2$)$_2$—COR$_9$ | — | — | — | Ph | Et | H |
| 40' | -(CH$_2$)$_2$—COR$_9$ | — | — | — | NH$_2$ | Et | H |
| 11-substituent | | | | | | | |
| 41' | —CH$_2$—CH$_3$ | — | — | — | — | H | H |
| 42' | -(CH$_2$)$_2$—COOR$_8$ | — | — | CH$_3$ | — | H | H |
| 43' | -(CH$_2$)$_2$—COOR$_8$ | — | — | H | — | H | H |
| 44' | —CH$_2$—CH(NR$_5$R$_6$)—COOR$_8$ | H | COCH$_3$ | CH$_3$ | — | H | H |
| 45' | —CH$_2$—CH(NR$_5$R$_6$)—COOR$_8$ | H | H | CH$_3$ | — | H | H |
| 46' | —CH$_2$—CH(NR$_5$R$_6$)—COOR$_8$ | H | H | H | — | H | H |
| 47' | —CH$_2$—CH(NR$_5$R$_6$)—COOR$_8$ | H | COCH$_3$ | H | — | H | H |
| 48' | -(CH$_2$)$_2$—COR$_9$ | — | — | — | CH$_3$ | H | H |
| 49' | -(CH$_2$)$_2$—COR$_9$ | — | — | — | Ph | H | H |
| 50' | -(CH$_2$)$_2$—COR$_9$ | — | — | — | NH$_2$ | H | H |
| 12-substituent | | | | | | | |
| 51' | —CH$_2$—CH$_3$ | — | — | — | — | H | 9-NH$_2$ |
| 52' | -(CH$_2$)$_2$—COOR$_8$ | — | — | CH$_3$ | — | H | 9-NH$_2$ |
| 53' | -(CH$_2$)$_2$—COOR$_8$ | — | — | H | — | H | 9-NH$_2$ |
| 54' | —CH$_2$—CH(NR$_5$R$_6$)—COOR$_8$ | H | COCH$_3$ | CH$_3$ | — | H | 9-NH$_2$ |

TABLE 2-continued

| Compound | | $R_5$ | $R_6$ | $R_8$ | $R_9$ | $R_4$ | X |
|---|---|---|---|---|---|---|---|
| 55' | —CH₂—CH(NR₅R₆)—COOR₈ | H | H | CH₃ | — | H | 9-NH₂ |
| 56' | —CH₂—CH(NR₅R₆)—COOR₈ | H | H | H | — | H | 9-NH₂ |
| 57' | —CH₂—CH(NR₅R₆)—COOR₈ | H | COCH₃ | H | — | H | 9-NH₂ |
| 58' | —(CH₂)₂—COR₉ | — | — | — | CH₃ | H | 9-NH₂ |
| 59' | —(CH₂)₂—COR₉ | — | — | — | Ph | H | 9-NH₂ |
| 60' | —(CH₂)₂—COR₉ | — | — | — | NH₂ | H | 9-NH₂ |
| 9-substituent | | | | | | | |
| 61' | —CH₂—CH₃ | — | — | — | — | H | 10-NH₂ |
| 62' | —(CH₂)₂—COOR₈ | — | — | CH₃ | — | H | 10-NH₂ |
| 63' | (CH₂)₂—COOR₈ | — | — | H | — | H | 10-NH₂ |
| 64' | —CH₂—CH(NR₅R₆)—COOR₈ | H | COCH₃ | CH₃ | — | H | 10-NH₂ |
| 65' | —CH₂—CH(NR₅R₆)—COOR₈ | H | H | CH₃ | — | H | 10-NH₂ |
| 66' | —CH₂—CH(NR₅R₆)—COOR₈ | H | H | H | — | H | 10-NH₂ |
| 67' | —CH₂—CH(NR₅R₆)—COOR₈ | H | COCH₃ | H | — | H | 10-NH₂ |
| 68' | —(CH₂)₂—COR₉ | — | — | — | CH₃ | H | 10-NH₂ |
| 69' | —(CH₂)₂—COR₉ | — | — | — | Ph | H | 10-NH₂ |
| 70' | —(CH₂)₂—COR₉ | — | — | — | NH₂ | H | 10-NH₂ |
| 12-substituent | | | | | | | |
| 71' | —CH₂—CH₃ | — | — | — | — | H | H |
| 72' | —(CH₂)₂—COOR₈ | — | — | CH₃ | — | H | H |
| 73' | —(CH₂)₂—COOR₈ | — | — | H | — | H | H |
| 74' | —CH₂—CH(NR₅R₆)—COOR₈ | H | COCH₃ | CH₃ | — | H | H |
| 75' | —CH₂—CH(NR₅R₆)—COOR₈ | H | H | CH₃ | — | H | H |
| 76' | —CH₂—CH(NR₅R₆)—COOR₈ | H | H | H | H | H | |
| 77' | —CH₂—CH(NR₅R₆)—COOR₈ | H | COCH₃ | H | — | H | H |
| 78' | —(CH₂)₂—COR₉ | — | — | — | CH₃ | H | H |
| 79' | —(CH₂)₂—COR₉ | — | — | — | Ph | H | H |
| 80' | —(CH₂)₂—COR₉ | — | — | — | NH₂ | H | H |
| 9-substituent | | | | | | | |
| 81' | —CH₂—CH₃ | — | — | — | — | H | 10-OH |
| 82' | —(CH₂)₂—COOR₈ | — | — | CH₃ | — | H | 10-OH |
| 83' | —(CH₂)₂—COOR₈ | — | — | H | — | H | 10-OH |
| 84' | —CH₂—CH(NR₅R₆)—COOR₈ | H | COCH₃ | CH₃ | — | H | 10-OH |
| 85' | —CH₂—CH(NR₅R₆)—COOR₈ | H | H | CH₃ | — | H | 10-OH |

TABLE 2-continued

| Compound | $R_5$ | $R_6$ | $R_8$ | $R_9$ | $R_4$ | X |
|---|---|---|---|---|---|---|
| 86' | —CH$_2$—CH(NR$_5$R$_6$)—COOR$_8$ | H | H | H | — | H | 10-OH |
| 87' | —CH$_2$—CH(NR$_5$R$_6$)—COOR$_8$ | H | COCH$_3$ | H | — | H | 10-OH |
| 88' | —(CH$_2$)$_2$—COR$_9$ | — | — | — | CH$_3$ | H | 10-OH |
| 89' | —(CH$_2$)$_2$—COR$_9$ | — | — | — | Ph | H | 10-OH |
| 90' | —(CH$_2$)$_2$—COR$_9$ | — | — | — | NH$_2$ | H | 10-OH |
| 91' | —CH$_2$—CH$_3$ | — | — | — | — | H | 10,11-OCH$_2$O— |
| 92' | —(CH$_2$)$_2$—COOR$_8$ | — | — | CH$_3$ | — | H | 10,11-OCH$_2$O— |
| 93' | —(CH$_2$)$_2$—COOR$_8$ | — | — | H | — | H | 10,11-OCH$_2$O— |
| 94' | —CH$_2$—CH(NR$_5$R$_6$)—COOR$_8$ | H | COCH$_3$ | CH$_3$ | — | H | 10,11-OCH$_2$O— |
| 95' | —CH$_2$—CH(NR$_5$R$_6$)—COOR$_8$ | H | H | CH$_3$ | — | H | 10,11-OCH$_2$O— |
| 96' | —CH$_2$—CH(NR$_5$R$_6$)—COOR$_8$ | H | H | H | — | H | 10,11-OCH$_2$O— |
| 97' | —CH$_2$—CH(NR$_5$R$_6$)—COOR$_8$ | H | COCH$_3$ | H | — | H | 10,11-OCH$_2$O— |
| 98' | —(CH$_2$)$_2$—COR$_9$ | — | — | — | CH$_3$ | H | 10,11-OCH$_2$O— |
| 99' | —(CH$_2$)$_2$—COR$_9$ | — | — | — | Ph | H | 10,11-OCH$_2$O— |
| 100' | —(CH$_2$)$_2$—COR$_9$ | — | — | — | NH$_2$ | H | 10,11-OCH$_2$O— |

9-substituent

| Compound | $R_5$ | $R_6$ | $R_8$ | $R_9$ | $R_4$ | X |
|---|---|---|---|---|---|---|
| 101' | —CH$_2$—CH$_3$ | — | — | — | — | H | 10-OCH$_3$ |
| 102' | —(CH$_2$)$_2$—COOR$_8$ | — | — | CH$_3$ | — | H | 10-OCH$_3$ |
| 103' | —(CH$_2$)$_2$—COOR$_8$ | — | — | H | — | H | 10-OCH$_3$ |
| 104' | —CH$_2$—CH(NR$_5$R$_6$)—COOR$_8$ | H | COCH$_3$ | CH$_3$ | — | H | 10-OCH$_3$ |
| 105' | —CH$_2$—CH(NR$_5$R$_6$)—COOR$_8$ | H | H | CH$_3$ | — | H | 10-OCH$_3$ |
| 106' | —CH$_2$—CH(NR$_5$R$_6$)—COOR$_8$ | H | H | H | — | H | 10-OCH$_3$ |
| 107' | —CH$_2$—CH(NR$_5$R$_6$)—COOR$_8$ | H | COCH$_3$ | H | — | H | 10-OCH$_3$ |
| 108' | —(CH$_2$)$_2$—COR$_9$ | — | — | — | CH$_3$ | H | 10-OCH$_3$ |
| 109' | —(CH$_2$)$_2$—COR$_9$ | — | — | — | Ph | H | 10-OCH$_3$ |
| 110' | —(CH$_2$)$_2$—COR$_9$ | — | — | — | NH$_2$ | H | 10-OCH$_3$ |

In Tables 1 and 2, the symbols Et and Ph stand respectively for ethyl and phenyl.

The present invention includes also in its scope a process for preparing the compounds of formula (I) as defined above, said process comprising 1) reacting a compound of formula (II)

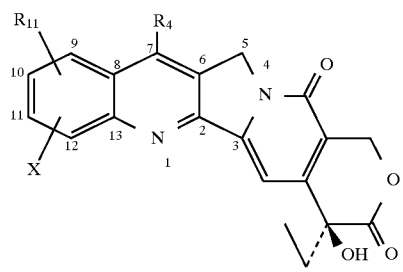

(II)

wherein
R$_{11}$ is a halogen atom, —OSO$_2$R$_{12}$ wherein R$_{12}$ is C$_1$–C$_5$ alkyl unsubstituted or substituted at the terminal carbon atom by one, two or three halogen atoms or an optionally substituted phenyl ring;

R$_4$ is hydrogen, C$_1$–C$_6$ alkyl, C$_3$–C$_7$ cycloalkyl or phenyl C$_1$–C$_6$ alkyl; and X is hydrogen, C$_1$–C$_6$ alkyl, C$_3$–C$_7$ cycloalkyl, C$_1$–C$_6$ alkoxy, C$_3$–C$_7$ cycloalkoxy, C$_1$–C$_6$ alkanoyloxy, benzoyloxy, amino hydroxy, nitro, halogen or it is a methylenedioxy group linked to the positions 10 and 11 of the molecule, with a compound of formula (III)

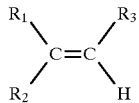
(III)

wherein
R$_1$, R$_2$ and R$_3$ are as defined under (a) or (b) below:
(a) R$_1$ and R$_2$ are each independently hydrogen; C$_1$–C$_4$ alkyl; C$_3$–C$_7$ cycloalkyl; phenyl C$_1$–C$_6$ alkyl; an optionally substituted phenyl ring; —NR$_5$R$_6$ wherein one of R$_5$ and R$_6$ is hydrogen, C$_1$–C$_6$ alkyl or benzyl and the other is hydrogen, C$_1$–C$_6$ alkanoyl, an optionally substituted benzoyl, phenyl C$_1$–C$_6$ alkanoyl, an optionally substituted C$_1$–C$_6$ alkoxycarbonyl, an optionally substituted phenoxycarbonyl or phenyl C$_1$–C$_6$ alkoxycarbonyl, or R$_5$ and R$_6$, combined together with the nitrogen atom to which they are linked, form a 4–7 membered saturated, optionally substituted, heteromonocyclic ring, represented by a group (G)

(G)

wherein W is —C=O, R$_7$ is hydrogen or C$_1$–C$_6$ alkyl and n is an integer of 2 to 5; COOR$_8$ wherein R$_8$ is C$_1$–C$_6$ alkyl, C$_3$–C$_7$ cycloalkyl or phenyl C$_1$–C$_6$ alkyl; or COR$_9$ wherein R$_9$ is C$_1$–C$_6$ alkyl, C$_3$–C$_7$ cycloalkyl, phenyl C$_1$–C$_6$ alkyl, an optionally substituted phenyl ring, NR$_{10}$R$_{11}$ wherein R$_{10}$ and R$_{11}$ are each independently hydrogen or C$_1$–C$_6$ alkyl; and
R$_3$ is hydrogen, C$_1$–C$_6$ alkyl or an optionally substituted phenyl; or
(b) R$_1$ and R$_3$, combined together, form a 5–8 membered, optionally substituted carbomonocyclic ring; and
R$_2$ is hydrogen, C$_1$–C$_4$ alkyl or C$_3$–C$_7$ cycloalkyl; so obtaining a compound of formula (I) wherein the symbol - - - - represents a double bond; and, if desired, 2) reducing a compound of formula (I) as obtained under step 1) into a corresponding compound of formula (I) wherein the symbol - - - - represents a single bond, and/or if desired, salifying a compound of formula (I).

The starting compounds of formula (II) have a 20 (S)-configuration which is retained through the process leading to the compounds of formula (I). The compounds of formula (II) are typically free of the corresponding 20 (R)-isomers.

However, said process may be applied to a racemic mixture of a compound of formula (II) and the corresponding 20 (R)-isomer. In that case, a racemic mixture of a compound of formula (I) and a 20 (R)-isomer of a compound of formula (I) is obtained. When one or more new stereogenic centers are created in one of the above mentioned steps, all the possible isomers, diastereoisomers, epimers, and geometric isomers, are included in the present disclosure.

The reaction reported under step 1) may be performed in a suitable solvent, in the presence of catalytic amounts, i.e. from 0.0001 to 0.2 molar equivalents, of a compound of formula ML$_q$L'$_r$ wherein
M represents Palladium, Nickel or Platinum.
L and L', which may be the same or different represent an anion such as, e.g. a halide or an acetate or a neutral molecule such as, e.g., a solvent molecule, a phosphine, a phosphite or a diamine; and
q and r may vary from 0 to 4,
provided that q+r is at least 1,
at a temperature of from about –20° C. to about 200° C., preferably from about 20° C. to about 100° C., for a time which may vary from few minutes to several days, such as, e.g., from 5 minutes to 3 days, preferably from about one hour to about one day, optionally in the presence of a suitable organic or inorganic base, and optionally in the presence of lithium halides, such as, e.g., LiCl, or LiBr.

Suitable solvents include, e.g., dimethylformamide (DMF), acetonitrile, dimethylsulphoxide (DMSO), CHCl$_3$, dioxane, tetrahydrofuran (THF) and mixtures thereof.

Suitable inorganic bases include, e.g., salts with alkali or alkaline earth metals, such as, for example, NaHCO$_3$, Na$_2$CO$_3$, or NaOAc.

Suitable organic bases may be, for example, trialkyalmines, such as, e.g., triethylamine or diisopropylethylamine; or heteroaromatic bases such as, e.g., pyridine, or 2,6,-C$_1$–C$_6$ alkyl substituted pyridines, such as, e.g., 2,6 lutidine.

Preferred groups which L and/or L' may represent are halides; acetates; phosphines such as, e.g., triphenylphosphine or chelating diphosphines, such as, e.g., bis (diphenylphosphino)methane, 1,2- and 1,3-bis (diphenylphosphino)propane, 1,4-bis(diphenylsphsphino)-butane or 1,1'-bis(diphenylphosphino)ferrocene (DPPF).

The molar ratio of transition metal atom with L and/or L' is in general from 1:1 to 1:4.

The reduction reported under item 2) may be performed reacting a compound of formula (I) as obtained under item 1) by using suitable reducing agents, in the presence of suitable catalysts.

Suitable catalysts for the abovesaid reduction are metals known to perform multiple bond reduction such as, e.g., Palladium, Platinum oxide, Platinum, Rhodium, Nickel or Ruthenium.

Suitable reducing agents for the abovesaid reduction are molecular hydrogen or hydrogen sources such as, for instance, triethylammonium formate, formic acid, tributyltin hydride, cyclohexadiene, etc., in a suitable solvent such as, e.g., dimethylformamide (DMF), CH$_3$OH, acetic acid, CHCl$_3$, dioxane, or mixtures thereof, at a temperature of from about 0° C. to about 100° C., for a time of from 1 hour to 3 days, at a pressure of from about 1 atm to about 100 atm.

The starting materials used in this disclosure are known compounds or may be obtained following known methods.

For instance, 9-halogeno camptothecin, 10-halogeno camptothecin, 11-halogeno camptothecin, and 12-halogeno camptothecin may be prepared according, to Sawada, S., et al., Chem. Pharm. Bull. 39, 3183–3188 (1991).

For instance, 10-hydroxy-9-halogeno camptothecin, 10-methoxy9-halogeno camptothecin, and 10,11-methylendioxy-9-halogeno camptothecin may be prepared starting from the corresponding 10 or 10,11 substituted 9-amino-derivatives, prepared by known procedures (see, for instance, Wall et al. J.Med.Chem. 1993, 36,2689–2700, or Wani et al. J. Med. Chem. 1986, 29, 2358–2363), and then following the above cited reference.

For instance, 9-trifluoromethansulfonyloxy camptothecin, 10-trifluoromethansulfonyloxy camptothecin, 11-trifluoromethansulfonyloxy camptothecin, 12-trifluoromethansulfonyloxy camptothecin, 10-hydroxy-9-trifluoromethansulfonyloxy camptothecin, 10-methoxy-9-trifluoromethansulfonyloxy camptothecin, 10,11-methylendioxy-9-trifluoromethansulfonyloxy camptothecin, 10-p-toluensulfonyloxy camptothecin, 11-p-toluensulfonyloxy camptothecin, 12-p-toluensulfonyloxy camptothecin, 10-hydroxy-9-p-toluensulfonyloxy camptothecin, 10-methoxy-9-p-toluensulfonyloxy camptothecin and 10,11-methylen-dioxy-9-p-toluensulfonyloxy camptothecin were prepared from the corresponding hydroxy derivatives obtained, in turn, as described in the references cited above, and treatment with suitable sulfonylating agents.

The compounds of the present invention are endowed with antitumor activity, for example against leukaemia and solid tumors such as, for example, colon and rectal tumors.

The antitumor activity of the compounds of the present invention is shown, for example, by the fact that they have been found to possess antileukaemic activity when tested according to the method described in: J.Med.Chem. 1993, 36, 2689, using the L1210 murine lymphoid leukemia model.

As an example, the activity of (E)-9-(2-methoxycarbonyl-ethenyl) camptothecin (internal code FCE 28681) and 9-(2-methoxycarbonyl-ethyl) camptothecin (internal code FCE 29559) were tested according to the following method (a).

The compounds were dissolved in dimethylsulfoxide (DMSO) at a final concentration of 0.5%. The percentage of DMSO solution does not affect the cellular growth.
Method (a): evaluation of cytotoxic activity L1210 murine leukemia cells were grown in vitro as a floated cells in RPMI 1640 medium supplemented with 10% fetal calf serum, 1% L-glutamine 200 mM, 1% of B-mercaptoethanol 1 mM, 100 UI/ml penicillin and 100 $\mu$g streptomycin. For assaying the cytotoxic activity, exponentially growing cells were seeded at the concentration of $5\times10^4$ cells/ml and exposed to graded doses of the compounds under evaluation for 48 h at 37° C. in an humidified atmosphere of 5% $CO_2$. The number of surviving cells was determined with a Coulter Counter; results are expressed as IC50 (dose causing 50% inhibition of cell growth in treated cultures relative to untreated controls after 48 h treatment) in this assay, (E)-9-(2-methoxycarbonyl-ethenyl) camptothecin (internal code FCE 28681) and 9-(2-methoxycarbonyl-ethyl) camptothecin (internal code FCE 29559) were tested and the obtained results are reported on Table 1 below.

TABLE 1

| COMPOUND | $IC_{50}$ (ng/ml) |
|---|---|
| FCE 28681 | 3.3 ± 1.8 |
| FCE 29559 | 2.7 ± 0.5 |

A human or animal body may thus be treated by a method which comprises the administration thereto of a pharmaceutically effective amount of a compound of formula (I) or salt thereof. The condition of the human or animal can thereby be improved. Pharmaceutical compositions containing the novel camptothecin analogues according to the invention are also within the scope of the present invention.

These pharmaceutical compositions may contain any quantity of a camptothecin analog which is effective to exhibit any antitumor activity in vivo. Mammalian such as humans are treatable with the inventive compositions. Typical in vivo doses within the scope of the invention are from 0.1–60 mg of camptothecin analog per kg of body weight. A particularly preferred range is 1–40 mg/kg.

There may also be included as part of the composition pharmaceutically compatible binding agents, and/or adjuvant materials. The active materials can also be mixed with other active materials which do not impair the desired action and/or supplement the desired action. The active materials according to the present invention can be administered by any route, for example, orally, parenterally, intravenously, intradermally, subcutaneously, or topically, in liquid or solid form.

A preferred mode of administration of the compounds of the invention is oral.

Oral compositions will generally include an inert diluent or an edible carrier. They may be enclosed in gelatin capsules or compressed into tablets. For the purpose of oral therapeutic administration, the aforesaid compounds may be incorporated with excipients and used in the form of tablets, capsules, elixirs, syrups and the like. These preparations should contain at least 0,1% of active compound but may be varied depending upon the particular form.

The tablets, pills, capsules, troches and the like may contain the following ingredients: a binder such as microcrystalline cellulose, gumtragacanth or gelatin; an excipient such as starch or lactose, a disintegrating agent such as alginic acid, Primogel, corn starch and the like; a lubricant such as magnesium stearate or Sterotes; a glidant such as colloidal silicon dioxide; a sweetening agent such as sucrose or saccharin or flavouring agent such as peppermint, methyl salicylate, or orange flavouring may be added. When the dosage unit form is a capsule, it may contain, in addition to material of the above type, a liquid carrier such as fatty oil. Other dosage unit forms may contain other various materials which modify the physical form of the dosage unit, for example, as coatings. Thus tablets or pills may be coated with sugar shellac, or other enteric coating agents.

A syrup may contain, in addition to the active compounds, sucrose as a sweetening agent and certain preservatives, dyes and colouring and flavours.

Material used in preparing these various compositions should be pharmaceutically pure and non toxic in the amount used.

For the purpose of parenteral therapeutic administration, the active ingredient may be incorporated into a solution or suspension.

The solutions or suspensions may also include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulphite; chelating agents such as ethylenediaminetetraacetic acid; buffers such as acetates, citrates or phosphates and agents for the adjustment of tonicity such as sodium chloride or dextrose. The parenteral preparation can be enclosed in ampoules, disposable syringes or multiple dose vials made of glass or plastic.

The dosage values will vary with the specific severity of the disease condition to be alleviated. Good results are achieved when the compounds described herein are administered to a subject requiring such treatment as an effective oral, parenteral or intravenous dose. It is to be understood that for any particular subject, specific dosage regimens should be adjusted to the individual need and the professional judgment of the person administering or supervising the administration of the aforesaid compound. It is to be further understood that the dosages set forth herein are exemplary only and they do not limit the scope or practice of the invention. The dosages may be administered at once, or may be divided into a number of smaller doses to be administered at varying intervals of time.

The following examples illustrates but do not limit the invention.

The number into bracket reported before the chemical name of the compounds prepared according to the following examples corresponds to the number given to the preferred compounds listed on pages 6–18 of the present specification.

PREPARATION OF THE STARTING MATERIALS

Method A:

9-bromo camptothecin 2.15 g of $NaNO_2$ in 40 mL of $H_2O$ were dropped at 5° C. into a solution of 9 g of 9-amino-camptothecin in 850 mL of 16% HBr. After 1 hr at r.t. the solution was dropped in a flask containing 19 g of CuBr in 200 mL of 16% HBr at 70° C. The reaction was allowed to stay at 70° C. for 2 hr, then it was poured in cold water. The precipitate was filtered and the mother liquors were extracted with $CH_2Cl_2$; the organic extract dried and evaporated was combined with the precipitate and purified by flash chromatography (eluent: $CH_2Cl_2/CH_3OH=95/5$) to give 8.19 g of the title product. (HPLC assay: 97.3%) $^1$H-NMR 400 MHz (DMSO-d6): d=8.87 (s, 1H), 8.20 (d, J=8.5, 1H), 8.06 (d, J=7.32, 1H), 7.81–7.75 (m, 1H), 7.35 (s, 1H), 6.53 (s, 1H), 5.42 (s, 2H), 5.32 (s, 2H), 1.89–1.82 (m, 2H), 0.87 (t, J=7.32, 3H). MS (FD): $M^+$=427.

By analogy starting from the corresponding amino derivatives, the following bromo derivatives were prepared:
10-bromo camptothecin;
11-bromo camptothecin;
12-bromo camptothecin;
10-hydroxy-9-bromo camptothecin;
10-methoxy-9-bromo camptothecin; and
10,11-methylendioxy-9-bromo camptothecin.

Method B:

10-trifluoromethansulfonyloxy camptothecin 1.25 g of 10-hydroxy camptothecin were dissolved in 35 mL of DMF and 2 mL of $Et_3N$ and 1.5 g of N,N-Bis-(trifluormethansulfonyl)-aniline were added. The solution was heated at 50° C. for 1 hr, then poured in water; the precipitate was filtered and the mother liquors were extracted with $CH_2Cl_2$. The organic extract, dried ($Na_2SO_4$) and evaporated, was combined with the precipitate and purified by flash chromatography (eluent: $CH_2Cl_2/CH_3OH=$ 98/2). 1 g of the title product was obtained.

(HPLC assay: 97%); $^1$H-NMR 400 MHz (DMSO-d6): d=8.81 (s, 1H), 8.43–8.32 (m, 2H), 7.99–7.94 (m, 1H), 7.36 (s, 1H), 6.54 (s, 1H), 5.42 (s, 2H), 5.32 (s, 2H), 1.90–1.81 (m, 2H), 0.86 (t, J=7.3 Hz, 3H). MS (FD): $M^+$=496

By analogy, starting from the corresponding nitro and amino derivatives, the following sulfonyl derivatives were prepared:
9-trifluoromethansulfonyloxy camptothecin;
11-trifluoromethansulfonyloxy camptothecin;
12-trifluoromethansulfonyloxy camptothecin;
10,11-methylendioxy-9-trifluoromethansulfonyloxy camptothecin;
10-p-toluensulfonyloxy camptothecin;
11-p-toluensulfonyloxy camptothecin;
12-p-toluensulfonyloxy camptothecin;
10-methoxy-9-p-toluensulfonyloxy camptothecin; and
10,11-methylendioxy-9-p-toluensulfonyloxy camptothecin.

EXAMPLE 1

12-vinyl camptothecin (65)

1 g of 12-Br-camptothecin was dissolved in 20 mL of DMF; in an Ar atmosphere, 0.72 mL of $Et_3N$, 3.61 mL of vinyltrimethylsilane, 0.071 g of DPPF and 0.026 g of $Pd(OAc)_2$ were added sequentially. The reaction mixture was heated at 100° C. for 1 hr and then treated with $CH_2Cl_2$ and water. The aqueous phase was extracted twice with $CH_2Cl_2$ and the organic extracts were collected, dried ($Na_2SO_4$), and evaporated. The residue was dissolved in 20 mL of $CH_2Cl_2$, 10 mL of $CF_3COOH$ were added and the solution was left at r.t. for 24 hr. The reaction was worked up as before and the product was purified by flash chromatography (eluent: $CH_2Cl_2/CH_3OH=95/5$) to give 0.59 g of the title product. (HPLC assay: 97%).

$^1$H-NMR 400 MHz (DMSO-d6): d=8.67 (s, 1H), 8.14–8.00 (m, 3H), 7.69 (t, J=7.9 Hz, 1H), 7.36 (s, 1H), 6.54 (s, 1H), 6.14 (dd, J=1.2, 17.9 Hz, 1H), 5.57 (d, J=12.3 Hz, 1H), 5.42 (s, 2H), 5.28 (s, 2H), 1.94–1.80 (m, 2H), 0.88 (t, J=7.0 Hz, 3H). MS (FD): $M^+$=374.

By analogy the following compounds were obtained (Table 1):
9-vinyl camptothecin (1);
7-ethyl-9-vinyl camptothecin (9);
10-vinyl camptothecin (17);
7-ethyl-10-vinyl camptothecin (25);
10-hydroxy-9-vinyl camptothecin (33);
10,11-methylendioxy-9-vinyl camptothecin (41);
10-methoxy-9-vinyl camptothecin (49);
11-vinyl camptothecin (57);
9-amino-10-vinyl camptothecin (73); and
7-ethyl-9-amino-10-vinyl camptothecin (81).

EXAMPLE 2

(Z)-12-(2-acetylamino-2-methoxycarbonyl-ethenyl) camptothecin (68)

2 g of 12-Br-camptothecin were dissolved in 40 mL of DMF; in an Ar atmosphere, 0.72 mL of $Et_3N$, 3.32 g of Methyl 2-acetamidoacrylate, 0.14 g of DPPF and 0.052 g of $Pd(OAc)_2$ were added sequentially. The reaction mixture was heated at 100° C. for 24 hr. The reaction mixture was cooled to room temperature, diluted with $CH_2Cl_2$ and washed with water. The organic extract was dried ($Na_2SO_4$) and the solvent removed under vacuo. The crude was purified by flash chromatography (eluent: $CH_2Cl_2/CH_3OH=$ 98/2) to give 1.72 g of the title product. (HPLC assay 97.4%); $^1$H-NMR 400 MHz (DMSO-d6) d=9.79 (s, 1H), 8.73 (s, 1H) 8.32 (s, 1H), 8.18 (d, J=7.03 Hz, 1H), 8.15 (d, J=7.91 Hz, 1H), 7.75 (t, J=7.62 Hz, 1H), 7.34 (s, 1H), 6.56 (s, 1H), 5.43 (s, 2H), 5.43 (s, 2H), 3.78 (s, 3H), 1.98 (s, 3H), 1.88 (m, 2H), 0.88 (t, J=7.3 Hz, 3H). MS (FD): $M^+$=489.

When a solution of (Z)-12-(2-acetylamino-2-methoxycarbonyl-ethenyl)camptothecin is allowed to stand at room temperature for 2 weeks, a 50/50 mixture of E and Z isomers is obtained.

By analogy the following compounds were obtained (Table 1):
10-(2-acetylamino-2-methoxycarbonyl-ethenyl) camptothecin (20);
10-(2-acetylamino-2-hydroxycarbonyl-ethenyl) camptothecin (21);
7-ethyl-10-(2-acetylamino-2-methoxycarbonyl-ethenyl) camptothecin (28);

7-ethyl-10-(2-acetylamino-2-hydroxycarbonyl-ethenyl) camptothecin (29);
10-hydroxy-9-(2-acetylamino-2-methoxycarbonyl-ethenyl) camptothecin (36);
10-hydroxy-9-(2-acetylamino-2-hydroxycarbonyl-ethenyl) camptothecin (37);
10,11-methylendioxy-9-(2-acetylamino-2-methoxycarbonyl-ethenyl)camptothecin (44);
10,11-methylendioxy-9-(2-acetylamino-2-hydroxycarbonyl-ethenyl)camptothecin (45);
10-methoxy-9-(2-acetylamino-2-methoxycarbonyl-ethenyl) camptothecin (52);
10-methoxy-9-(2-acetylamino-2-hydroxycarbonyl-ethenyl) camptothecin (53);
11-(2-acetylamino-2-methoxycarbonyl-ethenyl) camptothecin (60);
11-(2-acetylamino-2-hydroxycarbonyl-ethenyl) camptothecin (61);
12-(2-acetylamino-2-hydroxycarbonyl-ethenyl) camptothecin (69);
9-amino-10-(2-acetylamino-2-methoxycarbonyl-ethenyl) camptothecin (76);
9-amino-10-(2-acetylamino-2-hydroxycarbonyl-ethenyl) camptothecin (77);
7-ethyl-9-amino-10-(2-acetylamino-2-methoxycarbonyl-ethenyl)camptothecin (84); and
7-ethyl-9-amino-10-(2-acetylamino-2-hydroxycarbonyl-ethenyl)camptothecin (85).

EXAMPLE 3

(E)-12-(2-methoxycarbonyl-ethenyl)camptothecin (66)

5 g of 12-Br-camptothecin were dissolved in 50 mL of DMF; in an Ar atmosphere, 1.5 mL of Et$_3$N, 4.6 mL of Methyl acrylate, 0.28 g of DPPF and 0.11 g of Pd(OAc)$_2$ were added sequentially. The reaction was heated at 100° C. for 18 hr then worked up diluting with CH$_2$Cl$_2$ and washing twice with water. The organic phase was dried (Na$_2$SO$_4$) evaporated and the residue was purified by flash chromatography (eluent: CH$_2$Cl$_2$/CH$_3$OH=98/2) to give 4.1 g of the title product. (HPLC assay: 92.34%) $^1$H-NMR 400 MHz (DMSO-d6): d=8.94 (d, J=16.2 Hz, 1H), 8.73 (s, 1H), 8.39 (d, J=6.7 Hz, 1H), 8.21 (d, J=8.2 Hz, 1H), 7.75 (t, J=7.6, 1H), 7.36 (s, 1H), 7.00 (d, J=16.2 Hz, 1H), 6.59 (s, 1H), 5.43 (s, 2H), 5.30 (s, 2H), 3.80 (s, 3H), 1.88 (m, 2H), 0.89 (t, 3H). MS (FD): M$^+$=432.

By analom, the following compounds were obtained (Table 1):
11-(2-methoxycarbonyl-ethenyl)camptothecin (58);
11-(2-hydroxycarbonyl-ethenyl)camptothecin (59);
11-(3-oxo-but-1-enyl)camptothecin (62);
11-(3-oxo-3-phenyl-propenyl)camptothecin (63);
11-(2-aminocarbonyl-ethenyl)camptothecin (64);
12-(2-hydroxycarbonyl-ethenyl)camptothecin (67);
12-(3-oxo-but-1-enyl)camptothecin (70);
12-(3-oxo-3-phenyl-propenyl)camptothecin (71);
12-(2-aminocarbonyl-ethenyl)camptothecin (72);
9-amino-10-(2-methoxycarbonyl-ethenyl)camptothecin (74);
9-amino-10-(2-hydroxycarbonyl-ethenyl)camptothecin (75);
9-amino-10-(3-oxo-but-1-enyl)camptothecin (78);
9-amino-10-(3-oxo-3-phenyl-propenyl)camptothecin (79);
9-amino-10-(2-aminocarbonyl-ethenyl)camptothecin (80);
7-ethyl-9-amino-10-(2-methoxycarbonyl-ethenyl) camptothecin (82);
7-ethyl-9-amino-10-(2-hydroxycarbonyl-ethenyl) camptothecin (83);
7-ethyl-9-amino-10-(3-oxo-but-1-enyl)camptothecin (86);
7-ethyl-9-amino-10-(3-oxo-3-phenyl-propenyl) camptothecin (87); and
7-ethyl-9-amino-10-(2-aminocarbonyl-ethenyl) camptothecin (88).

EXAMPLE 4

12-(2-methoxycarbonyl-ethyl)camptothecin (52')

1 g of 12-(2-methoxycarbonyl-ethenyl)camptothecin was dissolved in 20 mL of DMF and hydrogenated in presence of 0.1 g of Pd/C at r.t. under 1 atm of H$_2$. The reaction mixture was filtered through a celite pad washing the celite thoroughly with DMF, the solvent was evaporated and the residue was purified by flash chromatography (eluent: CH$_2$Cl$_2$/CH$_3$OH=98/2) to give 0.82 g of the title product.

$^1$H-NMR 400 MHz (DMSO-d6): d=8.60 (s, 1H), 7.92 (dd, J=1.5, 8.2 Hz, 1H), 7.66 (dd, J=1.5, 7 Hz, 1H), 7.54 (dd, J=7, 8.2 Hz, 1H), 7.31 (s, 1H), 6.54 (s, 1H), 5.41 (s, 2H), 5.20 (m, 2H), 3.57 (s, 3H), 3.52–3.49 (m, 2H), 2.84–2.81 (m, 2H), 1.88–1.84 (m, 2H), 0.88 (t, J=7.3 Hz, 3H). MS (FD): M$^+$=434.

By analogy the following compounds were obtained (Table 2):
11-ethyl camptothecin (41');
11-(2-methoxycarbonyl-ethyl)camptothecin (42');
11-(2-hydroxycarbonyl-ethyl)camptothecin (43');
11-(3-oxo-butyl)camptothecin (48');
11-(3-oxo-3-phenyl-propyl)camptothecin (49');
11-(2-aminocarbonyl-ethyl)camptothecin (50');
9-amino-12-ethyl camptothecin (51');
9-amino-12-(2-methoxycarbonyl-ethyl)camptothecin (52');
9-amino-12-(2-hydroxycarbonyl-ethyl)camptothecin (53');
9-amino-12-(3-oxo-butyl)camptothecin (58');
9-amino-12-(3-oxo-3-phenyl-propyl)camptothecin (59');
9-amino-12-(2-aminocarbonyl-ethyl)camptothecin (60');
10-amino-9-ethyl camptothecin (61');
10-amino-9-(2-methoxycarbonyl-ethyl)camptothecin (62');
10-amino-9-(2-hydroxycarbonyl-ethyl)camptothecin (63');
10-amino-9-(3-oxo-butyl)camptothecin (68');
10-amino-9-(3-oxo-3-phenyl-3-one-propyl)camptothecin (69');
10-amino-9-(2-aminocarbonyl-ethyl)camptothecin (70');
12-ethyl camptothecin (71');
12-(2-hydroxycarbonyl-ethyl)camptothecin (73');
12-(3-oxo-butyl)camptothecin (78');
12-(3-oxo-3-phenyl-propyl)camptothecin (79');
12-(2-aminocarbonyl-ethyl)camptothecin (80');
10-hydroxy-9-ethyl camptothecin (81');
10-hydroxy-9-(2-methoxycarbonyl-ethyl)camptothecin (82');
10-hydroxy-9-(2-hydroxycarbonyl-ethyl)camptothecin (83');
10-hydroxy-9-(3-oxo-butyl)camptothecin (88');
10-hydroxy-9-(3-oxo-3-phenyl-3-one-propyl)camptothecin (89');
10-hydroxy-9-(2-aminocarbonyl-ethyl)camptothecin (90');
10-methoxy-9-ethyl camptothecin (101');
10-methoxy-9-(2-methoxycarbonyl-ethyl)camptothecin (102');
10-methoxy-9-(2-hydroxycarbonyl-ethyl)camptothecin (103');
10-methoxy-9-(3-oxo-butyl)camptothecin (108');
10-methoxy-9-(3-oxo-3-phenyl-propyl)camptothecin (109'); and
10-methoxy-9-(2-aminocarbonyl-ethyl)camptothecin (110').

EXAMPLE 5

12-[(2R,S)(2-acetylamino-2-methoxycarbonyl)-ethyl] camptothecin (74')

1 g of (Z)-12-(2-acetylamino-2-methoxycarbonyl-ethenyl)camptothecin was dissolved in DMF. After addition of 0.15 g of Pd/C, the product was hydrogenated at r.t. for 28 hr. The reaction mixture was filtered through a pad of celite and evaporated; the residue was purified by flash chromatography (eluent: $CH_2Cl_2/CH_3OH$) to give 0.89 g of the title product.

(HPLC assay: 96.7%) $^1$H-NMR 400 MHz (DMSO-d6): d=8.66 (s, 1H), 8.49–8.43 (m, 1H), 7.99 (d, J=7.33 Hz, 1H), 7.63–7.60 (m, 2H), 7.42 (s, 1/2H), 7.40 (s, 1/2H), 6.56 (s, 1/2H), 6.54 (s, 1/2H), 5.42 (s, 2H), 5.30 (s, 2H), 4.75–4.66 (m, 1H), 3.96–3.88 (m, 1H), 3.55 (s, 1.5H), 3.49 (s, 1.5H), 3.36–3.31 (m, 1H), 1.81–1.87 (m, 2H), 1.77 (s, 1.5H), 1.75 (s, 1.5H), 0.92–0.94 (m, 3H). MS (FD): $M^+$=491

By analogy the following compounds may be obtained (Table 2):

9-[(2-acetylamino-2-methoxycarbonyl]-ethyl)camptothecin (4');
9-[(2-amino-2-methoxycarbonyl]-ethyl)camptothecin (5');
9-[(2-amino-2-hydroxycarbonyl)-ethyl]camptothecin (6');
9-[(2-acetylamino-2-hydroxycarbony)-ethyl]camptothecin (7');
7-ethyl-9-[(2-acetylamino-2-methoxycarbonyl]-ethyl) camptothecin (14');
7-ethyl-9-[(2-amino-2-methoxycarbonyl]-ethyl) camptothecin (15');
7-ethyl-9-[(2-amino-2-hydroxycarbonyl)-ethyl] camptothecin (16');
7-ethyl-9-[(2-acetylamino-2-hydroxycarbonyl)-ethyl] camptothecin (17');
10-[(2-acetylamino-2-methoxycarbonyl]-ethyl) camptothecin (24');
10-[(2-amino-2-methoxycarbonyl]-ethyl)camptothecin (25');
10-[(2-amino-2-hydroxycarbonyl)-ethyl]camptothecin (26');
10-[(2-acetylamino-2-hydroxycarbony)-ethyl]camptothecin (27');
7-ethyl-10-[(2-acetylamino-2-methoxycarbonyl]-ethyl) camptothecin (34');
7-ethyl-10-[(2-amino-2-methoxycarbonyl]-ethyl) camptothecin (35');
7-ethyl-10-[(2-amino-2-hydroxycarbonyl)-ethyl] camptothecin (36');
7-ethyl-10-[(2-acetylamino-2-hydroxycarbony)-ethyl] camptothecin (37');
11-[(2-acetylamino-2-methoxycarbonyl]-ethyl) camptothecin (44');
11-[(2-amino-2-methoxycarbonyl]-ethyl)camptothecin (45');
11-[(2-amino-2-hydroxycarbonyl)-ethyl]camptothecin (46');
11-[(2-acetylamino-2-hydroxycarbonyl)-ethyl] camptothecin (47');
9-amino-12-[(2-acetylamino-2-methoxycarbonyl]-ethyl) camptothecin (54');
9-amino-12-[(2-amino-2-methoxycarbonyl]-ethyl) camptothecin (55');
9-amino-12-[(2-amino-2-hydroxycarbonyl)-ethyl] camptothecin (56');
9-amino-12-[(2-acetylamino-2-hydroxycarbonyl)-ethyl] camptothecin (57');
10-amino-9-[(2-acetylamino-2-methoxycarbonyl]-ethyl) camptothecin (64');
10-amino-9-[(2-amino-2-methoxycarbonyl]-ethyl) camptothecin (65');
10-amino-9-[(2-amino-2-hydroxycarbonyl)-ethyl] camptothecin (66');
10-amino-9-[(2-acetylamino-2-hydroxycarbony)-ethyl] camptothecin (67');
12-[(2-amino-2-methoxycarbonyl]-ethyl)camptothecin (75');
12-[(2-amino-2-hydroxycarbonyl)-ethyl]camptothecin (76');
12-[(2-acetylamino-2-hydroxycarbony)-ethyl]camptothecin (77');
10-hydroxy-9-[(2-acetylamino-2-methoxycarbonyl]-ethyl) camptothecin (84');
10-hydroxy-9-[(2-amino-2-methoxycarbonyl]-ethyl) camptothecin (85');
10-hydroxy-9-[(2-amino-2-hydroxycarbonyl)-ethyl] camptothecin (86');
10-hydroxy-9-[(2-acetylamino-2-hydroxycarbony)-ethyl] camptothecin (87');
10,11-methylendioxy-9-[(2-acetylamino-2-methoxycarbonyl]-ethyl)-camptothecin (94');
10,11-methylendioxy-9-[(2-amino-2-methoxycarbonyl]-ethyl)camptothecin (95');
10,11-methylendioxy-9-[(2-amino-2-hydroxycarbonyl)-ethyl]camptothecin (96');
10,11-methylendioxy-9-[(2-acetylamino-2-hydroxycarbony)-ethyl]-camptothecin (97');
10-methoxy-9-[(2-acetylamino-2-methoxycarbonyl]-ethyl) camptothecin (104');
10-methoxy-9-[(2-amino-2-methoxycarbonyl]-ethyl) camptothecin (105');
10-methoxy-9-[(2-amino-2-hydroxycarbonyl)-ethyl] camptothecin (106'); and
10-methoxy-9-[(2-acetylamino-2-hydroxycarbony)-ethyl] camptothecin (107').

EXAMPLE 7

(Z)-9-(2-acetylamino-2-methoxycarbonyl-ethenyl) camptothecin (4)

5 g of 9-Br-camptothecin were dissolved in 50 mL of DMF; in an Ar atmosphere, 1.8 mL of $Et_3N$, 8.3 g of Methyl 2-acetamidoacrylate, 0.35 g of DPPF and 0.13 g of $Pd(OAc)_2$ were added sequentially. The reaction mixture was heated at 100° C. for 7 hr and then taken up with $CH_2Cl_2$ and water. The organic extract was dried ($Na_2SO_4$), the solvent was evaporated and the residue was purified by flash chromatography (eluent: $CH_2Cl_2/CH_3OH$=98/2) to give 4.89 g of the title product. (HPLC assay: 98.7%)

$^1$H-NMR 400 MHz (DMSO-d6): d=9.63 (s, 1H), 8.73 (s, 1H), 8.16 (d, J=8.54 Hz, 1H), 7.89–7.85 (m, 1H), 7.77 (d, J=7.26, 1H), 7.62 (s, 1H), 7.34 (s, 1H), 6.52 (s, 1H), 5.41 (s, 2H), 5.25 (s, 2H), 3.76 (s, 3H), 1.87–1.83 (m, 5H), 0.86 (t, J=7.26, 3H). MS (FD): $M^+$=489

When a solution of (Z)-9-(2-acetylamino-2-methoxycarbonyl-ethenyl) camptothecin is allowed to stand at r.t. for 2 weeks, a 50/50 mixture of E and Z isomers is obtained. The $^1$H-NMR spectrum of (E)-9-(2-acetylamino-2-methoxycarbonyl-ethenyl) camptothecin is:

d=10.32 (s, 1H), 8.74 (s, 1H), 8.09 (d, J=8.79, 1H), 7.80–7.76 (m, 1H), 7.63 (s, 1H), 7.37–7.34 (m, 2H), 6.53 (s, 1H), 5.42 (s, 2H), 5.28 (s, 2H), 3.42 (s, 3H), 2.02 (s, 3H), 1.89–1.82 (m, 2H), 0.87 (t, J=7.26, 3H).

By analogy the following compounds were prepared (Table 1):

9-(2-acetylamino-2-hydroxycarbonyl-ethenyl)camptothecin (5);
7-ethyl-9-(2-acetylamino-2-methoxycarbonyl-ethenyl) camptothecin (12); and
7-ethyl-9-(2-acetylamino-2-hydroxycarbonyl-ethenyl) camptothecin (13).

EXAMPLE 8

(E)-9-(2-methoxycarbonyl-ethenyl)camptothecin (2)

1 g of 9-Br-camptothecin was dissolved in 11 mL of DMF; 0.3 mL of Et$_3$N, 0.92 mL of Methyl acrylate, 0.056 g of DPPF, 0.022 g of Pd(OAc)$_2$ were added sequentially under an Ar atmosphere. The reaction mixture was heated at 100° C.; after 3 hr the reaction is over and a white yellowish precipitate is present. The precipitate is filtered and washed twice with DMF and twice with Et$_2$O. The product is crystallized (CHCl$_3$/DMF) to give 0.58 g of the title product. (HPLC assay: 95.59%)

$^1$H-NMR 400 MHz (DMSO-d6): d=9.07 (s, 1H), 8.45 (d, J=15.5 Hz, 1H), 8.23 (d, J=8.5 Hz, 1H), 8.14 (d, J=7.1, 1H), 7.88 (dd, J=7.6 Hz, J'=8.2 Hz, 1H), 7.34 (s, 1H), 6.80 (d, J=15.8 Hz, 1H), 6.53 (s, 1H), 5.42 (s, 2H), 5.27 (s, 2H), 3.79 (s, 3H), 1.86 (m, 2H), 0.87 (t, 3H). MS (FD): M$^+$=432.

By analogy the following compounds were prepared (Table 1):

9-(2-hydroxycarbonyl-ethenyl)camptothecin (3);
9-(2-aminocarbonyl-ethenyl)camptothecin (8);
9-(3-oxo-but-1-enyl)camptothecin (6);
9-(3-oxo-3-phenyl-propenyl)camptothecin (7);
7-ethyl-9-(2-methoxycarbonyl-ethenyl)camptothecin (10);
7-ethyl-9-(2-hydroxycarbonyl-ethenyl)camptothecin (11);
7-ethyl-9-(3-oxo-but-1-enyl)camptothecin (14);
7-ethyl-9-(3-oxo-3-phenyl-propenyl)camptothecin (15);
7-ethyl-9-(2-aminocarbonyl-ethenyl)camptothecin (16);
10,11-methylendioxy-9-(2-methoxycarbonyl-ethenyl) camptothecin (42);
10,11-methylendioxy-9-(2-hydroxycarbonyl-ethenyl) camptothecin (43);
10,11-methylendioxy-9-(3-oxo-but-1-enyl)camptothecin (46);
10,11-methylendioxy-9-(3-oxo-3-phenyl-propenyl) camptothecin (47);
10,11-methylendioxy-9-(2-aminocarbonyl-ethenyl) camptothecin (48);
10-methoxy-9-(2-methoxycarbonyl-ethenyl)camptothecin (50);
10-methoxy-9-(2-hydroxycarbonyl-ethenyl)camptothecin (51);
10-methoxy-9-(3-oxo-but-1-enyl)camptothecin (54);
10-methoxy-9-(3-oxo-3-phenyl-propenyl)camptothecin (55); and
10-methoxy-9-(2-aminocarbonyl-ethenyl)camptothecin (56).

EXAMPLE 9

9-(2-methoxycarbonyl-ethyl)camptothecin (2')

1.4 g of (E)-9-(2-methoxycarbonyl-ethenyl)camptothecin are dissolved in 400 mL of DMF, 0.3 g of Pd/C are added and the mixture is hydrogenated at r.t. (1 atm H$_2$) for 3 hr. The reaction mixture is filtered and the solvent is evaporated. The residue is purified by flash chromatography (eluent: CH$_2$Cl$_2$/CH$_3$OH=98/2) to give 1.2 g of the title product.

$^1$H-NMR 400 MHz (DMSO-d6): d=8.89 (s, 1H), 8.03 (d, J=8.49 Hz, 1H), 7.79–7.73 (m, 1H), 7.55 (d, J=7.03, 1H), 7.33 (s, 1H), 6.51 (s, 1H), 5.42 (s, 2H), 5.28 (s, 2H), 3.59 (s, 3H), 3.42–3.36 (m, 2H), 2.88–2.77 (m, 2H), 1.91–1.80 (m, 2H), 0.87 (t, J=7.33, 3H). MS (FD): M$^+$=434.

By analogy the following compounds were prepared (Table 2):

9-ethyl camptothecin (1');
9-(2-hydroxycarbonyl-ethyl)camptothecin (3');
9-(3-oxo-butyl)camptothecin (8');
9-(3-oxo-3-phenyl-propyl)camptothecin (9');
9-(2-aminocarbonyl-ethyl)camptothecin (10');
7-ethyl-9-ethyl camptothecin (11');
7-ethyl-9-(2-methoxycarbonyl-ethyl)camptothecin (12');
7-ethyl-9-(2-hydroxycarbonyl-ethyl)camptothecin (13');
7-ethyl-9-(3-oxo-butyl)camptothecin (18');
7-ethyl-9-(3-oxo-3-phenyl-propyl)camptothecin (19');
7-ethyl-9-(2-aminocarbonyl-ethyl)camptothecin (20');
10-ethyl camptothecin (21');
10-(2-methoxycarbonyl-ethyl)camptothecin (22');
10-(2-hydroxycarbonyl-ethyl)camptothecin (23');
10-(3-oxo-butyl)camptothecin (28');
10-(3-oxo-3-phenyl-propyl)camptothecin (29');
10-(2-aminocarbonyl-ethyl)camptothecin (30');
7-ethyl-10-ethyl camptothecin (31');
7-ethyl-10-(2-methoxycarbonyl-ethyl)camptothecin (32');
7-ethyl-10-(2-hydroxycarbonyl-ethyl)camptothecin (33');
7-ethyl-10-(3-oxo-butyl)camptothecin (38');
7-ethyl-10-(3-oxo-3-phenyl-propyl)camptothecin (39');
7-ethyl-10-(2-aminocarbonyl-ethyl)camptothecin (40');
10,11-methylendioxy-9-ethyl camptothecin (91');
10,11-methylendioxy-9-(2-methoxycarbonyl-ethyl) camptothecin (92');
10,11-methylendioxy-9-(2-hydroxycarbonyl-ethyl) camptothecin (93');
10,11-methylendioxy-9-(3-oxo-butyl)camptothecin (98');
10,11-methylendioxy-9-(3-oxo-3-phenyl-propyl) camptothecin (99'); and
10,11-methylendioxy-9-(2-aminocarbonyl-ethyl) camptothecin (100').

EXAMPLE 10

(E)-10-(2-methoxycarbonyl-ethenyl)camptothecin (18)

1 g of 10-trifluoromethansulfonyloxy camptothecin was dissolved in 10 mL of DMF; in an Ar atmosphere, 0.31 mL of Et$_3$N, 0.91 mL of Methyl acrylate, 0.062 g of DPPF and 0.023 g of Pd(OAc)$_2$ were added sequentially. The reaction was heated at 80° C. for 24 hr then worked up diluting with CH$_2$Cl$_2$ and washing twice with brine. The organic phase was dried (Na$_2$SO$_4$) evaporated and the residue was purified by flash chromatography (eluent: CH$_2$Cl$_2$/CH$_3$OH=99/1) to give 0.5 g of the title product. (HPLC assay: 97%)

$^1$H-NMR 400 MHz (DMSO-d6): d=8.65 (s, 1H), 8.42 (s, 1H), 8.24 (d, J=9.0 Hz, 1H), 8.14 (d, J=9.0 Hz, 1H), 7.86 (d, J=16.1 Hz, 1H), 7.34 (s, 1H), 6.87 (d, J=16.1 Hz, 1H), 6.53 (s, 1H), 5.41 (s, 2H), 5.28 (s, 2H), 3.76 (s, 3H), 1.88–1.82 (m, 2H), 0.86 (t, J=7.3 Hz, 3H). MS (FD): M$^+$=432.

By analogy the following compounds were prepared (Table 1):

10-(2-hydroxycarbonyl-ethenyl)camptothecin (19);
10-(3-oxo-but-1-enyl)camptothecin (22);
10-(3-oxo-3-phenyl-propenyl)camptothecin (23);
10-(2-aminocarbonyl-ethenyl)camptothecin (24);
7-ethyl-10-(2-methoxycarbonyl-ethenyl)camptothecin (26);
7-ethyl-10-(2-hydroxycarbonyl-ethenyl)camptothecin (27);
7-ethyl-10-(3-oxo-but-1-enyl)camptothecin (30);
7-ethyl-10-(3-oxo-3-phenyl-propenyl)camptothecin (31);
7-ethyl-10-(2-aminocarbonyl-ethenyl)camptothecin (32);
10-hydroxy-9-(2-methoxycarbonyl-ethenyl)camptothecin (34);
10-hydroxy-9-(2-hydroxycarbonyl-ethenyl)camptothecin (35);
10-hydroxy-9-(3-oxo-but-1-enyl)camptothecin (38);
10-hydroxy-9-(3-oxo-3-phenyl-propenyl)camptothecin (39); and
10-hydroxy-9-(2-aminocarbonyl-ethenyl)camptothecin (40).

We claim:
1. A camptothecin compound represented by formula (I):

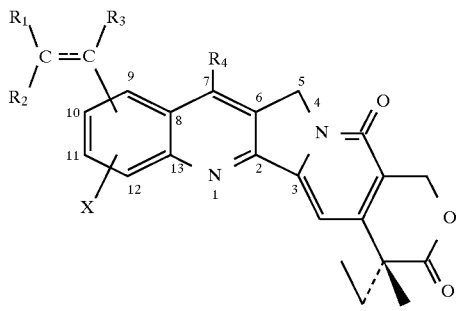

wherein
the symbol - - - - represents a double bond;
$R_1$, $R_2$ and $R_3$ are as defined under (a) or (b) below:
(a) $R_1$ and $R_2$ are each, independently,
hydrogen;
$C_1$–$C_4$ alkyl;
$C_3$–$C_7$ cycloalkyl;
phenyl $C_1$–$C_6$ alkyl;
a phenyl group, wherein said phenyl group is optionally substituted with one member selected from the group consisting of $C_1$–$C_6$ alkyl, $C_1$–$C_6$ alkoxy, $C_1$–$C_6$ alkanoyloxy, nitro and halogen;
—$NR_5R_6$, wherein one of $R_5$ and $R_6$ is hydrogen, $C_1$–$C_6$ alkyl or benzyl and the other is hydrogen, $C_1$–$C_6$ alkanoyl, $C_1$–$C_6$ alkoxycarbonyl, trichloroethoxycarbonyl, benzoyl, wherein the phenyl ring of said benzoyl is optionally substituted with one member selected from the group consisting of $C_1$–$C_6$ alkyl, $C_1$–$C_6$ alkoxy, $C_1$–$C_6$ alkanoyloxy, nitro and halogen, phenyl $C_1$–$C_6$ alkanoyl, phenoxycarbonyl, wherein the phenyl ring of said phenoxycarbonyl is optionally substituted with one member selected from the group consisting of $C_1$–$C_6$ alkyl, $C_1$–$C_6$ alkoxy, $C_1$–$C_6$ alkanoyloxy, nitro and halogen, or phenyl $C_1$–$C_6$ alkoxycarbonyl,
or $R_5$ and $R_6$, combined together with the nitrogen atom to which they are linked, form a 4–6 membered saturated heteromonocyclic ring represented by the formula (G):

wherein W is —C=O, $R_7$ is hydrogen or $C_1$–$C_6$ alkyl and n is an integer of 2 to 4;
—$COOR_8$ wherein $R_3$ is hydrogen, $C_1$–$C_6$ alkyl, $C_3$–$C_7$ cycloalkyl or phenyl $C_1$–$C_6$ alkyl; or
—$COR_9$, wherein $R_9$ is $C_1$–$C_6$ alkyl, $C_3$–$C_7$ cycloalkyl, phenyl $C_1$–$C_6$ alkyl, or phenyl, wherein said phenyl is optionally substituted with one member selected from the group consisting of $C_1$–$C_6$ alkyl, $C_1$–$C_6$ alkoxy, $C_1$–$C_6$ alkanoyloxy, nitro and halogen, or $NR_{10}R_{11}$ wherein $R_{10}$ and $R_{11}$ are each, independently, hydrogen or $C_1$–$C_6$ alkyl; and
$R_3$ is hydrogen, $C_1$–$C_6$ alkyl or a phenyl group, wherein said phenyl group is optionally substituted with one member selected from the group consisting of $C_1$–$C_6$ alkyl, $C_1$–$C_6$ alkoxy, $C_1$–$C_6$ alkanoyloxy, nitro and halogen; or (b) $R_1$ and $R_3$, combined together, form a 5–8 membered carbomonocyclic ring; and
$R_2$ is hydrogen, $C_1$–$C_4$ alkyl or $C_3$–$C_7$ cycloalkyl;
$R_4$ is hydrogen, $C_1$–$C_6$ alkyl, or phenyl $C_1$–$C_6$ alkyl;
X is hydrogen, $C_1$–$C_6$ alkyl, $C_3$–$C_7$ cycloalkyl, $C_1$–$C_6$ alkoxy, $C_3$–$C_7$ cycloalkoxy, $C_1$–$C_6$ alkanoyloxy, benzoyloxy, amino, hydroxy, or nitro, or a pharmaceutically acceptable salt thereof,
with the proviso that $R^1$, $R^2$ and $R^3$ are each simultaneously not a tert-butyl group or a substituted or unsubstituted phenyl group.
2. The camptothecin compound of claim 1 or a pharmaceutically acceptable salt thereof, wherein
$R_1$ and $R_2$ are each, independently,
hydrogen;
—$NR_5R_6$ wherein one of $R_5$ and $R_6$ is hydrogen and the other is hydrogen, $C_1$–$C_6$ alkanoyl, benzoyl, wherein the phenyl ring of said benzoyl is optionally substituted with at one member selected from the group consisting of $C_1$–$C_6$ alkyl, $C_1$–$C_6$ alkoxy, $C_1$–$C_6$ alkanoyloxy, nitro and halogen, phenyl $C_1$–$C_6$ alkanoyl, $C_1$–$C_6$ alkoxycarbonyl, phenoxycarbonyl or phenyl $C_1$–$C_6$ alkoxycarbonyl;
—$COOR_8$ wherein $R_8$ is hydrogen or $C_1$–$C_6$ alkyl; or
—$COR_9$ wherein $R_9$ is $C_1$–$C_6$ alkyl, unsubstituted phenyl, or $NR_{10}R_{11}$ wherein $R_{10}$ and $R_{11}$ are both hydrogen;
$R_3$ is hydrogen;
$R_4$ is hydrogen or $C_1$–$C_6$ alkyl;
X is hydrogen, hydroxy, amino, or $C_1$–$C_6$ alkoxy.
3. The camptothecin compound of claim 2 or a pharmaceutically acceptable salt thereof, wherein one of $R_5$ and $R_6$ is hydrogen and the other is hydrogen $C_1$–$C_6$ alkanoyl, unsubstituted benzoyl, phenyl $C_1$–$C_6$ alkanoyl, $C_1$–$C_6$ alkoxycarbonyl, phenoxycarbonyl or phenyl $C_1$–$C_6$ alkoxycarbonyl.
4. The camptothecin compound of claim 1 or a pharmaceutically acceptable salt thereof, wherein
$R_1$, $R_2$ and $R_3$ are as defined under (a) or (b) below:
(a) $R_1$ and $R_2$ are each, independently,
hydrogen;
$C_1$–$C_4$ alkyl;
$C_3$–$C_7$ cycloalkyl;
phenyl $C_1$–$C_6$ alkyl;
a phenyl group, wherein said phenyl group is optionally substituted with one member selected from the group consisting of $C_1$–$C_6$ alkyl, $C_1$–$C_6$ alkoxy, $C_1$–$C_6$ alkanoyloxy and nitro;
—$NR_5R_6$, wherein one of $R_5$ and $R_6$ is hydrogen, $C_1$–$C_6$ alkyl or benzyl and the other is hydrogen, $C_1$–$C_6$ alkanoyl, $C_1$–$C_6$ alkoxycarbonyl, trichloroethoxycarbonyl, benzoyl, wherein the phenyl ring of said benzoyl is optionally substituted with one member selected from the group consisting of $C_1$–$C_6$ alkyl, $C_1$–$C_6$ alkoxy, $C_1$–$C_6$ alkanoyloxy and nitro, phenyl $C_1$–$C_6$ alkanoyl, phenoxycarbonyl, wherein the phenyl ring of said phenoxycarbonyl is optionally substituted with one member selected from the group consisting of $C_1$–$C_6$ alkyl, $C_1$–$C_6$ alkoxy, $C_1$–$C_6$ alkanoyloxy and nitro, or phenyl $C_1$–$C_6$ alkoxycarbonyl,
or $R_5$ and $R_6$, combined together with the nitrogen atom to which they are linked, form a 4–6 membered saturated heteromonocyclic ring represented by the formula (G):

wherein W is —C=O, $R_7$ is hydrogen or $C_1$–$C_6$ alkyl and n is an integer of 2 to 4;

—COOR$_8$ wherein $R_3$ is hydrogen, $C_1$–$C_6$ alkyl, $C_3$–$C_7$ cycloalkyl or phenyl $C_1$–$C_6$ alkyl; or —COR$_9$, wherein $R_9$ is $C_1$–$C_6$ alkyl, $C_3$–$C_7$ cycloalkyl, phenyl $C_1$–$C_6$ alkyl, or phenyl, wherein said phenyl is optionally substituted with one member selected from the group consisting of $C_1$–$C_6$ alkyl, $C_1$–$C_6$ alkoxy, $C_1$–$C_6$ alkanoyloxy and nitro, or NR$_{10}$R$_{11}$ wherein $R_{10}$ and $R_{11}$ are each, independently, hydrogen or $C_1$–$C_6$ alkyl; and $R_3$ is hydrogen, $C_1$–$C_6$ alkyl or a phenyl group, wherein said phenyl group is optionally substituted with one member selected from the group consisting of $C_1$–$C_6$ alkyl, $C_1$–$C_6$ alkoxy, $C_1$–$C_6$ alkanoyloxy and nitro; or (b) $R_1$ and $R_3$, combined together, form a 5–8 membered carbomonocyclic ring; and $R_2$ is hydrogen, $C_1$–$C_4$ alkyl or $C_3$–$C_7$ cycloalkyl; $R_4$ is hydrogen, $C_1$–$C_6$ alkyl, or phenyl $C_1$–$C_6$ alkyl;

X is hydrogen, $C_1$–$C_6$ alkyl, $C_3$–$C_7$ cycloalkyl, $C_1$–$C_6$ alkoxy, $C_3$–$C_7$ cycloalkoxy, $C_1$–$C_6$ alkanoyloxy, benzoyloxy, amino, hydroxy, or nitro.

5. The camptothecin compound of claim 1 or a pharmaceutically acceptable salt thereof, wherein $R_1$, $R_2$ and $R_3$ are as defined under (a) or (b) below:

(a) $R_1$ and $R_2$ are each, independently, hydrogen;
$C_1$–$C_4$ alkyl;
$C_3$–$C_7$ cycloalkyl;
phenyl $C_1$–$C_6$ alkyl;
a phenyl group, wherein said phenyl group is optionally substituted with one member selected from the group consisting of $C_1$–$C_6$ alkyl, $C_1$–$C_6$ alkoxy, $C_1$–$C_6$ alkanoyloxy and halogen;

—NR$_5$R$_6$, wherein one of $R_5$ and $R_6$ is hydrogen, $C_1$–$C_6$ alkyl or benzyl and the other is hydrogen, $C_1$–$C_6$ alkanoyl, $C_1$–$C_6$ alkoxycarbonyl, trichloroethoxycarbonyl, benzoyl, wherein the phenyl ring of said benzoyl is optionally substituted with one member selected from the group consisting of $C_1$–$C_6$ alkyl, $C_1$–$C_6$ alkoxy, $C_1$–$C_6$ alkanoyloxy and halogen, phenyl $C_1$–$C_6$ alkanoyl, phenoxycarbonyl, wherein the phenyl ring of said phenoxycarbonyl is optionally substituted with one member selected from the group consisting of $C_1$–$C_6$ alkyl, $C_1$–$C_6$ alkoxy, $C_1$–$C_6$ alkanoyloxy and halogen, or phenyl $C_1$–$C_6$ alkoxycarbonyl, or $R_5$ and $R_6$, combined together with the nitrogen atom to which they are linked, form a 4–6 membered saturated heteromonocyclic ring represented by the formula (G):

wherein W is —C=O, $R_7$ is hydrogen or $C_1$–$C_6$ alkyl and n is an integer of 2 to 4;

—COOR$_8$ wherein $R_3$ is hydrogen, $C_1$–$C_6$ alkyl, $C_3$–$C_7$ cycloalkyl or phenyl $C_1$–$C_6$ alkyl; or —COR$_9$, wherein $R_9$ is $C_1$–$C_6$ alkyl, $C_3$–$C_7$ cycloalkyl, phenyl $C_1$–$C_6$ alkyl, or phenyl, wherein said phenyl is optionally substituted with one member selected from the group consisting of $C_1$–$C_6$ alkyl, $C_1$–$C_6$ alkoxy, $C_1$–$C_6$ alkanoyloxy and halogen, or NR$_{10}$R$_{11}$ wherein $R_{10}$ and $R_{11}$ are each, independently, hydrogen or $C_1$–$C_6$ alkyl; and $R_3$ is hydrogen, $C_1$–$C_6$ alkyl or a phenyl group, wherein said phenyl group is optionally substituted with one member selected from the group consisting of $C_1$–$C_6$ alkyl, $C_1$–$C_6$ alkoxy, $C_1$–$C_6$ alkanoyloxy and halogen; or (b) $R_1$ and $R_3$, combined together, form a 5–8 membered carbomonocyclic ring; and $R_2$ is hydrogen, $C_1$–$C_4$ alkyl or $C_3$–$C_7$ cycloalkyl; $R_4$ is hydrogen, $C_1$–$C_6$ alkyl, $C_3$–$C_7$ cycloalkyl or phenyl $C_1$–$C_6$ alkyl;

X is hydrogen, $C_1$–$C_6$ alkyl, $C_3$–$C_7$ cycloalkyl, $C_1$–$C_6$ alkoxy, $C_3$–$C_7$ cycloalkoxy, $C_1$–$C_6$ alkanoyloxy, benzoyloxy, amino, hydroxy, or nitro.

6. The camptothecin compound of claim 1 or a pharmaceutically acceptable salt thereof, wherein at least one of $R_1$ and $R_2$ are hydrogen;

$R_3$ is hydrogen;

$R_4$ is hydrogen or $C_1$–$C_6$ alkyl; and

X is hydrogen, $C_1$–$C_6$ alkyl, $C_3$–$C_7$ cycloalkyl, $C_1$–$C_6$ alkoxy, $C_3$–$C_7$ cycloalkoxy, $C_1$–$C_6$ alkanoyloxy, benzoyloxy, amino, hydroxy, or nitro.

7. The camptothecin compound of claim 1, which is 9-vinyl camptothecin, (E)-9-(2-methoxycarbonyl-ethenyl)camptothecin, 9-(2-hydroxycarbonyl-ethenyl)camptothecin, (Z)-9-(2-acetylamino-2-methoxycarbonyl-ethenyl) camptothecin, 9-(2-acetylamino-2-hydroxycarbonyl-ethenyl) camptothecin, 9-(3-oxo-but-1-enyl)camptothecin, 9-(3-oxo-3-phenyl-propenyl)camptothecin, 9-(2-aminocarbonyl-ethenyl)camptothecin, 7-ethyl-9-vinyl camptothecin, 7-ethyl-9-(2-methoxycarbonyl-ethenyl)camptothecin, 7-ethyl-9-(2-hydroxycarbonyl-ethenyl)camptothecin, 7-ethyl-9-(2-acetylamino-2-methoxycarbonyl-ethenyl) camptothecin, 7-ethyl-9-(2-acetylamino-2-hydroxycarbonyl-ethenyl) camptothecin, 7-ethyl-9-(3-oxo-but-1-enyl)camptothecin, 7-ethyl-9-(3-oxo-3-phenyl-propenyl)camptothecin, 7-ethyl-9-(2-aminocarbonyl-ethenyl)camptothecin, 10-vinyl camptothecin, (E)-10-(2-methoxycarbonyl-ethenyl)camptothecin, 10-(2-hydroxycarbonyl-ethenyl)camptothecin, 10-(2-acetylamino-2-methoxycarbonyl-ethenyl) camptothecin, 10-(2-acetylamino-2-hydroxycarbonyl-ethenyl) camptothecin, 10-(3-oxo-but-1-enyl)camptothecin, 10-(3-oxo-3-phenyl-propenyl)camptothecin, 10-(2-aminocarbonyl-ethenyl)camptothecin,
7-ethyl-10-vinyl camptothecin,
7-ethyl-10-(2-methoxycarbonyl-ethenyl)camptothecin,
7-ethyl-10-(2-hydroxycarbonyl-ethenyl)camptothecin,
7-ethyl-10-(2-acetylamino-2-methoxycarbonyl-ethenyl) camptothecin,
7-ethyl-10-(2-acetylamino-2-hydroxycarbonyl-ethenyl) camptothecin,
7-ethyl-10-(3-oxo-but-1-enyl)camptothecin,
7-ethyl-10-(3-oxo-3-phenyl-propenyl)camptothecin,
7-ethyl-10-(2-aminocarbonyl-ethenyl)camptothecin,
10-hydroxy-9-vinyl camptothecin,
10-hydroxy-9-(2-methoxycarbonyl-ethenyl) camptothecin,
10-hydroxy-9-(2-hydroxycarbonyl-ethenyl) camptothecin,
10-hydroxy-9-(2-acetylamino-2-methoxycarbonyl-ethenyl)camptothecin,
10-hydroxy-9-(2-acetylamino-2-hydroxycarbonyl-ethenyl)camptothecin,
10-hydroxy-9-(3-oxo-but-1-enyl)camptothecin,
10-hydroxy-9-(3-oxo-3-phenyl-propenyl)camptothecin,
10-hydroxy-9-(2-aminocarbonyl-ethenyl)camptothecin,
10-methoxy-9-vinyl camptothecin,
10-methoxy-9-(2-methoxycarbonyl-ethenyl) camptothecin,
10-methoxy-9-(2-hydroxycarbonyl-ethenyl) camptothecin,
10-methoxy-9-(2-acetylamino-2-methoxycarbonyl-ethenyl)camptothecin,
10-methoxy-9-(2-acetylamino-2-hydroxycarbonyl-ethenyl)camptothecin,
10-methoxy-9-(3-oxo-but-1-enyl)camptothecin,
10-methoxy-9-(3-oxo-3-phenyl-propenyl)camptothecin,
10-methoxy-9-(2-aminocarbonyl-ethenyl)camptothecin,
11-vinyl camptothecin,
11-(2-methoxycarbonyl-ethenyl)camptothecin,
11-(2-hydroxycarbonyl-ethenyl)camptothecin,
11-(2-acetylamino-2-methoxycarbonyl-ethenyl) camptothecin,
11-(2-acetylamino-2-hydroxycarbonyl-ethenyl) camptothecin,
11-(3-oxo-but-1-enyl)camptothecin,
11-(3-oxo-3-phenyl-propenyl)camptothecin,
11-(2-aminocarbonyl-ethenyl)camptothecin,
12-vinyl camptothecin,
(E)-12-(2-methoxycarbonyl-ethenyl)camptothecin,
12-(2-hydroxycarbonyl-ethenyl)camptothecin,
(Z)-12-(2-acetylamino-2-methoxycarbonyl-ethenyl) camptothecin,
12-(2-acetylamino-2-hydroxycarbonyl-ethenyl) camptothecin,
12-(3-oxo-but-1-enyl)camptothecin,
12-(3-oxo-3-phenyl-propenyl)camptothecin,
12-(2-aminocarbonyl-ethenyl)camptothecin,
9-amino-10-vinyl camptothecin,
9-amino-10-(2-methoxycarbonyl-ethenyl)camptothecin,
9-amino-10-(2-hydroxycarbonyl-ethenyl)camptothecin,
9-amino-10-(2-acetylamino-2-methoxycarbonyl-ethenyl) camptothecin,
9-amino-10-(2-acetylamino-2-hydroxycarbonyl-ethenyl) camptothecin,
9-amino-10-(3-oxo-but-1-enyl)camptothecin,
9-amino-10-(3-oxo-3-phenyl-propenyl)camptothecin,
9-amino-10-(2-aminocarbonyl-ethenyl)camptothecin,
7-ethyl-9-amino-10-vinyl camptothecin,
7-ethyl-9-amino-10-(2-methoxycarbonyl-ethenyl) camptothecin,
7-ethyl-9-amino-10-(2-hydroxycarbonyl-ethenyl) camptothecin,
7-ethyl-9-amino-10-(2-acetylamino-2-methoxycarbonyl-ethenyl)camptothecin,
7-ethyl-9-amino-10-(2-acetylamino-2-hydroxycarbonyl-ethenyl)camptothecin,
7-ethyl-9-amino-10-(3-oxo-but-1-enyl)camptothecin,
7-ethyl-9-amino-10-(3-oxo-3-phenyl-propenyl) camptothecin,
7-ethyl-9-amino-10-(2-aminocarbonyl-ethenyl) camptothecin, or a pharmaceutically acceptable salt thereof.

8. The compound of claim 1, or a pharmaceutically acceptable salt thereof, which is (E)-9-(2-methoxycarbonyl-ethenyl)camptothecin.

9. A pharmaceutical composition, comprising an anti-tumor and/or anti-leukemic effective amount of the camptothecin compound of claim 1 or a pharmaceutically acceptable salt thereof and a pharmaceutically acceptable carrier and/or diluent.

10. The composition of claim 9, comprising at least 0.1% by weight of the camptothecin compound or a pharmaceutically acceptable salt thereof.

11. A method of treating leukemia, comprising administering to a patient in need thereof an anti-leukemic effective amount of the camptothecin compound of claim 1 or a pharmaceutically acceptable salt thereof.

12. The method of claim 11, wherein 0.1 to 60 mg of the camptothecin compound or a pharmaceutically acceptable salt thereof per kg of the body weight of the patient is administered per day.

13. The method of claim 11, wherein 1 to 40 mg of the camptothecin compound or a pharmaceutically acceptable salt thereof per kg of the body weight of the patient is administered per day.

* * * * *